(12) United States Patent
Seki et al.

(10) Patent No.: US 11,946,910 B2
(45) Date of Patent: Apr. 2, 2024

(54) TRIAZOLINEDIONE ADDUCT, METHOD FOR PRODUCING TRIAZOLINEDIONE ADDUCT, METHOD FOR PRODUCING ENE COMPOUND, AND METHOD FOR ANALYZING ENE COMPOUND

(71) Applicants: TOKUYAMA CORPORATION, Yamaguchi (JP); JEOL Ltd., Tokyo (JP)

(72) Inventors: Masahiko Seki, Yamaguchi (JP); Seketsu Fukuzawa, Tokyo (JP); Masaki Takiwaki, Tokyo (JP)

(73) Assignees: Tokuyama Corporation, Yamaguchi (JP); Jeol Ltd., Tokyo (JP)

( * ) Notice: Subject to any disclaimer, the term of this patent is extended or adjusted under 35 U.S.C. 154(b) by 484 days.

(21) Appl. No.: 16/973,306

(22) PCT Filed: Jun. 11, 2019

(86) PCT No.: PCT/JP2019/023166
§ 371 (c)(1),
(2) Date: Dec. 8, 2020

(87) PCT Pub. No.: WO2019/240143
PCT Pub. Date: Dec. 19, 2019

(65) Prior Publication Data
US 2021/0253587 A1     Aug. 19, 2021

(30) Foreign Application Priority Data

Jun. 12, 2018 (JP) ................. 2018-112195
Jun. 12, 2018 (JP) ................. 2018-112196

(51) Int. Cl.
*G01N 30/06* (2006.01)
*C07D 487/08* (2006.01)
*G01N 33/82* (2006.01)

(52) U.S. Cl.
CPC ........... *G01N 30/06* (2013.01); *C07D 487/08* (2013.01); *G01N 33/82* (2013.01); *G01N 2030/067* (2013.01)

(58) Field of Classification Search
CPC ............................ C07D 487/08; C07D 487/04
See application file for complete search history.

(56) References Cited

U.S. PATENT DOCUMENTS

| 2011/0301063 A1 | 12/2011 | Netzel et al. |
| 2018/0088137 A1 | 3/2018 | Higashi et al. |
| 2018/0136240 A1 | 5/2018 | Higashi et al. |
| 2021/0253587 A1 | 8/2021 | Seki et al. |

FOREIGN PATENT DOCUMENTS

| EP | 3301453 A1 | 4/2018 |
| JP | 2015166740 A | 9/2015 |
| JP | 2018054459 A | 4/2018 |
| JP | 2018081023 A | 5/2018 |
| WO | 2019-240143 A1 | 12/2019 |

OTHER PUBLICATIONS

Ogawa, S. et al., "A Novel Cookson-Type Reagent for Enhancing Sensitivity and Specificity in Assessment of Infant Vitamin D Status Using Liquid Chromatography/Tandem Mass Spectrometry," Rapid Common. Mass Spectrom., 2013, vol. 27, pp. 2453-2460.
Ogawa, S. et al., "Comparative Evaluation of New Cookson-Type Reagents for LC/ESI-MS/MS Assay of 25-Hydroxyvitamin D3 in Neonatal Blood Samples," Biomed. Chromatgr., 30(2016) 938-945.
Ogawa, S. et al., "Enhancing Analysis Throughput, Sensitivity and Specificity INLC/ESI-MS/MS Assay of Plasma 25-Hydroxyvitamin D3 By Derivatization With Triplex4-(4-Dimethylaminophenyl)-1,2,4-Triazoline-3,5-Dione(Daptad)Isotopologues," J.Pharm. Biomed. Anal., 136(2017) 126-133.
K. D. Bruycker, et al., "Triazolinediones as Highly Enabling Synthetic Tools," Chem. Rev., 116(2016) 3919-3974.
Kiselev, V. D. et al., "Features of the Diels-Alder Reaction Between 9, 10-Diphenylanthracene and 4-Phenyl-1, 2, 4-Triazoline-3, 5-Dione", Russian Journal of Physical Chemistry A, 2014, vol. 88(12), pp. 2073-2080.
Kiselev, Vladimir D. et al., "Why Can the Diels-Alder Reaction of 9, 10-Disphenylanthracene With 4-Phenyl-1, 2, 4-Triazoline-3, 5-Dione Pass by an Abnormal Way?", Mendeleev Communications,2013, vol. 23(4), pp. 235-236.
Roy, Nabarun et al., "Dynamic Covalent Chemistry: A Facile Room-Temperature, Reversible, Diels-Alder Reaction Between Anthracene Derivatives and N-Phenyltriazolinedione", Chemistry—An Asian journal, 2011, vol. 6(9), pp. 2419-2425.
Ford Jackson W., et al., "Solvent Effects on the Kinetics of a Diels-Alder Reaction in Gas-Expanded Liquids", Industrial & Engineering Chemistry Research, 2008, vol. 47 (3), pp. 632-637.

(Continued)

*Primary Examiner* — Jennifer Wecker
*Assistant Examiner* — Michelle Adams
(74) *Attorney, Agent, or Firm* — HOGAN LOVELLS US LLP

(57) ABSTRACT

Provided are a stable triazolinedione adduct, a method for producing the same, a method for producing an ene compound, and a method for analyzing an ene compound. A triazolinedione adduct that is stable until the time of use and can be reacted while reverting to a triazolinedione compound at the time of use. Specifically, a triazolinedione adduct represented by formula (1). (In the formula, $R^1$ is an organic group, and A is a fused ring of three or more rings including at least one aromatic ring.)

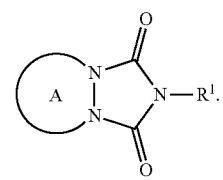

(1)

12 Claims, No Drawings

(56) References Cited

OTHER PUBLICATIONS

Werner Stefan, et al., "Fluorous Dienophiles are Powerful Diene Scavengers in Diels-Alder Reactions", Organic Letters, 2003, vol. 5 (18), pp. 3293-3296.
Menard Cecilia, et al., Ph3BiC03: "A Mild Reagent for in Situ Oxidation of Urazoles to Triazolinediones", Tetrahedron Letters, 2003, vol. 44 (35), pp. 6591-6593.
Mallakpour Shadpour E., et al., "Synthesis of New Heterocycli Compounds via Cycloaddition Reaction", Indian Journal of Chemistry, Section B: Organic Chemistry Including Medicinal Chemistry, 2002, vol. 41B(4), p. 812-816.
Thompson R. Lee, et al., "Rate Variations of a Hetero-Diels-Alder Reaction in Supercritical Fluid CO2", Industrial & Engineering Chemistry Research, 1999, vol. 38 (11), pp. 4220-4225.
Angermund Klaus, et al., "Thermal and Photochemical Reactions of Naphtho[L,2,3,4-Def]Chrysene With 4-Phenyl-1,2,4-Triazol Ine-3, 5-Dione", Chemische Berichte, 1988, vol. 121 (9), pp. 1647-1650.
Klobucar W. Dirk, et al., "Thermal Retrograde [2+2] Aromatization of Caged Bicyclo[4. 2.0] Octa-2,4-Diene Derivatives", Journal of Organic Chemistry, 1981, vol. 46 (13), pp. 2680-2683.
Burrage Martin E., et al., "Substituent and Solvent Effects on the Diels-Alder Reactions of Triazolinediones", Journal of the Chemical Society, Perkin Transactions 2: Physical Organic Chemistry, 1975, vol. 12, pp. 1325-1334.
Meehan Scott, et al., "A New Synthesis of Diazenes(Azoalkanes) Using 4-(S,S-Dimethylsulfoximino)-1,2,4-Triazoline-3,5-Dione. The Construction of Diazenes From Amino Nitrenes via Base-Induced Sulfoximine Cleavage", Journal of Organic Chemistry, 1997, vol. 62 (11), pp. 3779-3781.
Sauer Juergen, et al., "Diels-Alder Reactions. VIII. 4-Phenyl-1,2,4-Triazoline-3,5-Dione as a Dienophile", Chemische Berichte, 1967, vol. 100 (2), pp. 678-684.
Shimada, Kazutake et al., "High-Performance Liquid Chromatography/Mass Spectrometry of Vitamin D Compounds Employing Derivatization With Cookson-Type Reagents", Bunseki Kagaku, 2002, vol. 51 No. 7, pp. 487-493 (2002).
Cookson, Richard C. et al., "Diels-Alder Reactions of 4-Pheny 1-1, 2, 4-Triazoline-3, 5-Dione", Journal of the Chemical Society [Section] C: Organic, 1967, vol. 19, pp. 1905-1909.
Fernandez-Herrera, Maria A. et al., "A Convenient Methodology for the in Situ Oxidation of 4-Substituted Urazoles. Setting up a One-Pot Procedure for the Efficient Protection of Dienes", Heterocycles, 2013, vol. 87 (3), pp. 571-582.
Chatani, Hitoshi et al., "Contribution of the Proton Affinity in Cookson-Type Reagents Pretreating the Analytes to Improve the Detection Efficiency of Steroid Derivatives in ESI/MS Analysis", The 10th Annual meeting of Japan Society for Molecular Science, Lecture program abstracts, Aug. 31, 2016, 3P098.
Seki, M. et al. "A Novel Caged Cookson-Type Reagent Toward a Practical Vitamin D Derivatization Method for Mass Spectrometric Analyses," Rapid Commun Mass Spectrom. 2020;34:e8648. First published Nov. 12, 2019; including supporting information (Year: 2019).
Office Action Corresponding to U.S. Appl. No. 17/065,221 dated Feb. 24, 2023.
Kiselev, V.D. et al. "Kinetic and equilibrium parameters of [4+2] cycloaddition reaction of 2,6-dimethylnaphthalene with 4-phenyl-1,2,4-triazoline-3,5-dione," Russian Chemical Bulletin, International Edition, vol. 63, No. 3, pp. 770-771, Mar. 2014 (Year: 2014).
Office Action issued in the related U.S. Appl. No. 17/065,221, dated Jul. 12, 2023.

TRIAZOLINEDIONE ADDUCT, METHOD FOR PRODUCING TRIAZOLINEDIONE ADDUCT, METHOD FOR PRODUCING ENE COMPOUND, AND METHOD FOR ANALYZING ENE COMPOUND

This application is a U.S. National Phase under 35 U.S.C. § 371 of International Application PCT/JP2019/023166 filed on Jun. 11, 2019, which are incorporated herein in their entirety. This application also claims priority to Japanese Patent Application No. 2018-112195, filed on Jun. 12, 2018 and Japanese Patent Application No. 2018-112196, filed on Jun. 12, 2018. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a triazolinedione adduct, a method for producing the triazolinedione adduct, a method for producing an ene compound and a method for analyzing the ene compound.

BACKGROUND ART

There has recently been an increased need for analysis of vitamin D and vitamin D metabolites in blood. With regard to an analysis method of vitamin D and the vitamin D metabolites, a method has been proposed in which the vitamin D and the vitamin D metabolites are derivatized using a Cookson-type derivatization reagent and subsequently the derivative is analyzed (see Patent Document 1 and Non-Patent Documents 1 to 4).

Specifically, the Cookson-type derivatization reagent causes a Diels-Alder reaction with a diene derivative such as vitamin D to proceed extremely rapidly under mild conditions, to give an ene compound quantitatively (see, Non-Patent Documents 1 to 4). Utilizing this reaction characteristic, vitamin D and the like, which are per se difficult to be quantitatively determined, are reacted with the Cookson-type derivatization reagent to convert vitamin D and the like to an ene compound having higher analysis sensitivity, and thereafter the ene compound is quantified.

Examples of the aforementioned Cookson-type derivatization reagent include triazolinedione compounds such as PTAD (4-phenyl-1,2,4-triazoline-3,5-dione) and DAPTAD (4-(4'-dimethylaminophenyl)-1,2,4-triazoline-3,5-dione).

Patent Document 1: Japanese Unexamined Patent Application, Publication No. 2015-166740
Non-Patent Document 1: S. Ogawa, et al., Rapid Commun. Mass Spectrom, 27(2013) 2453-2460
Non-Patent Document 2: S. Ogawa, et al., Biomed. Chromatgr., 30(2016) 938-945
Non-Patent Document 3: S. Ogawa, et al., J. Pharm. Biomed. Anal., 136(2017) 126-133
Non-Patent Document 4: K. D. Bruycker, et al., Chem. Rev., 116(2016) 3919-3974

DISCLOSURE OF THE INVENTION

Problems to be Solved by the Invention

However, the triazolinedione compounds were unstable and accompanied by a high ratio of degradation during the process of isolation. The handling property as a compound was also low, because the stability after isolation was also low. Therefore, in order to handle a triazolinedione compound as a raw material for production or a quantitative reagent, a higher stability has been required.

The present invention was made in view of the above background and an object of the present invention is to provide a triazolinedione adduct having stability and a method for producing the same, as well as a method for producing an ene compound using the triazolinedione adduct and a method for analyzing a diene compound.

Another object of the present invention is to provide a method for producing an ene compound derived from a triazolinedione compound with high stability, using a triazolidinedione compound which is a precursor of the triazolinedione compound.

Means for Solving the Problems

The triazolinedione compound is known to reversibly undergo Diels-Alder reaction with a polycyclic aromatic hydrocarbon such as anthracene to give an adduct (see, e.g., N. Roy, et al., Chem. Asian. J., 6 (2011) pp. 2419-2425; V. D. Kiseleva, et al., Russ. J. Phys. Chem. A, 88 (2014) pp. 2073-2080; and the like). That is, the triazolinedione adduct once obtained undergoes a retrospective reaction to the starting materials, that is, the triazolinedione compound and polycyclic aromatic hydrocarbon, by heating (retro-Diels-Alder reaction).

The present inventors have focused on the above characteristics and have found that the stability of a triazolinedione compound can be secured by converting an unstable triazolinedione compound into a stable adduct and carrying out reaction while reverting the adduct to the triazolinedione compound at the time of use, thus having completed the present invention.

Further, the present inventors have found that if the triazolinedione compound is generated in a system by using a triazolidinedione compound which is a precursor of the triazolinedione compound, and then the generated triazolinedione compound is immediately reacted with a diene, the ene compound can be produced in a highly stable manner, thereby completing the present invention.

That is, a first aspect of the present invention relates to a triazolinedione adduct represented by the following formula (1):

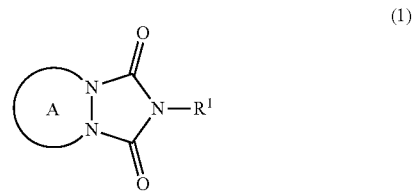

in which $R^1$ represents an organic group and A represents a fused ring of three or more rings comprising at least one aromatic ring.

$R^1$ in the formula (1) may represent a substituted phenyl group having a dialkylamino group or a dialkylaminoalkyl group, or an unsubstituted phenyl group.

The triazolinedione adduct may be a triazolinedione adduct represented by the following formula (2):

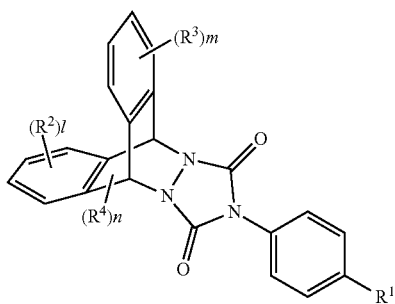

(2)

in which R¹ represents an organic group; R², R³, and R⁴ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and n is an integer of 0 to 2.

The triazolinedione adduct may be a triazolinedione adduct represented by the following formula (3):

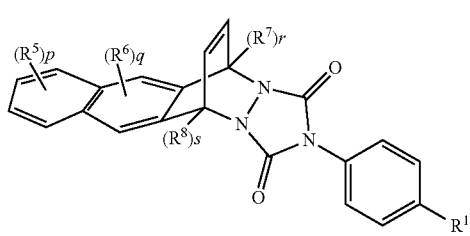

(3)

in which R¹ represents an organic group; R⁵, R⁶, R⁷, and R⁸ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; p is an integer of 0 to 4; q is an integer of 0 to 2; and r and s are integers of 0 or 1.

Another aspect of the present invention relates to a method for producing a triazolinedione adduct including subjecting a triazolinedione compound and a fused ring compound having at least two aromatic rings to a Diels-Alder reaction to obtain the triazolinedione adduct, in which the triazolinedione compound is represented by the following formula (4):

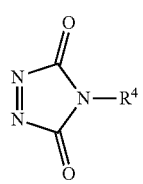

(4)

in which R¹ represents an organic group.

The method for producing a triazolinedione adduct may further include a purification step of purifying the triazolinedione adduct.

Another aspect of the present invention relates to a method for producing a triazolinedione adduct, including reacting a triazolidinedione compound with a fused ring compound having at least two aromatic rings in the presence of an oxidizing agent to obtain the triazolinedione adduct, in which the triazolidinedione compound is represented by the following formula (7):

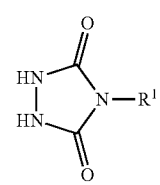

(7)

in which R¹ represents an organic group.

The oxidizing agent may be a hypervalent iodine compound.

The oxidizing agent may be a hypervalent iodine compound represented by the following formula (8):

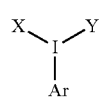

(8)

in which X and Y together represent an oxygen atom, or X and Y each independently represent a group selected from the group consisting of a hydroxy group, an alkoxy group, an acyloxy group, an acylamino group, a tosylamino group, a mesylamino group, a sulfonyloxy group, and a halogen group; and Ar represents a group selected from the group consisting of a phenyl group, a heterocyclic group, and a phenyl group substituted with an alkyl group, an alkoxy group, a halogen group, etc.

The method for producing the triazolinedione adduct may further include a purification step of purifying the triazolinedione adduct.

Another aspect of the present invention relates to a method for producing an ene compound, including reacting a triazolinedione adduct with a diene compound to obtain the ene compound, in which the triazolinedione adduct is represented by the following formula (1):

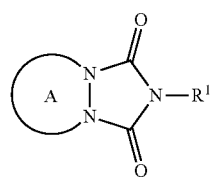

(1)

in which R¹ represents an organic group and A represents a fused ring having three or more rings including at least one aromatic ring; and in which the diene compound is represented by the following formula (5):

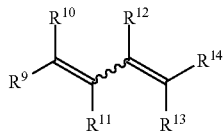

(5)

in which $R^9$, $R^{10}$, $R^{11}$, $R^{12}$, $R^{13}$, and $R^{14}$ each independently represent a group selected from the group consisting of an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^9$, $R^{10}$, $R^{11}$, $R^{12}$, $R^{13}$, and $R^{14}$ are optionally combined with one another; and in which the ene compound is represented by the following formula (6):

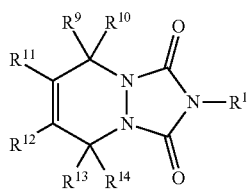

(6)

in which $R^1$ is as defined in the formula (1); and $R^9$, $R^{10}$, $R^{11}$, $R^{12}$, $R^{13}$ and $R^{14}$ are as defined in the formula (5).

Another aspect of the present invention relates to a method for analyzing an ene compound, including reacting a triazolinedione adduct with a diene compound to obtain the ene compound and analyzing the ene compound, in which the triazolinedione adduct is represented by the following formula (1):

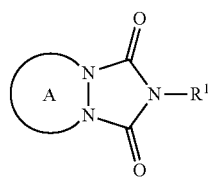

(1)

in which $R^1$ represents an organic group and A represents a fused ring having three or more rings including at least one aromatic ring;

in which the diene compound is represented by the following formula (5):

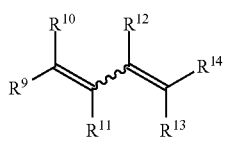

(5)

in which $R^9$, $R^{10}$, $R^{11}$, $R^{12}$, $R^{13}$, and $R^{14}$ each independently represent a group selected from the group consisting of an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^9$, $R^{10}$, $R^{11}$, $R^{12}$, $R^{13}$, and $R^{14}$ are optionally combined with one another; and in which the ene compound is represented by the following formula (6):

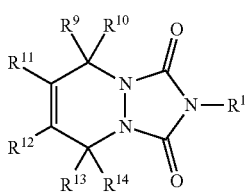

(6)

in which $R^1$ is as defined in the formula (1) and $R^9$, $R^{10}$, $R^{11}$, $R^{12}$, $R^{13}$ and $R^{14}$ are as defined in the formula (5).

The analysis may be a method using high performance liquid chromatography.

The diene compound may be vitamin D3 or 25-hydroxyvitamin D3.

Another aspect of the present invention relates to a method for producing an ene compound, including reacting a triazolidinedione compound with a diene compound in the presence of an oxidizing agent to obtain the ene compound, in which the triazolidinedione compound is represented by the following formula (7):

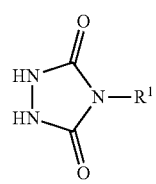

(7)

in which $R^1$ represents an organic group;

in which the diene compound is represented by the following formula (5):

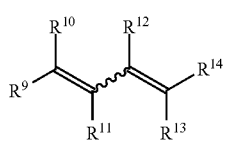

(5)

in which $R^9$, $R^{10}$, $R^{11}$, $R^{12}$, $R^{13}$, and $R^{14}$ each independently represent a group selected from the group consisting of an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^9$, $R^{10}$, $R^{11}$, $R^{12}$, $R^{13}$, and $R^{14}$ are optionally combined with one another; and in which the ene compound is represented by the following formula (6):

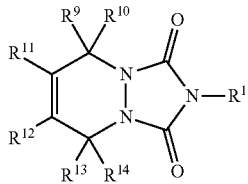

(6)

in which $R^1$ is as defined in the formula (7); and $R^9$, $R^{10}$, $R^{11}$, $R^{12}$, $R^{13}$ and $R^{14}$ are as defined in the formula (5).

The oxidizing agent may be a hypervalent iodine compound.

The oxidizing agent may be a hypervalent iodine compound represented by the following formula (8):

(8)

in which X and Y together represent an oxygen atom, or X and Y each independently represent a group selected from the group consisting of a hydroxy group, an alkoxy group, an acyloxy group, an acylamino group, a tosylamino group, a mesylamino group, a sulfonyloxy group, and a halogen group; and Ar represents a group selected from the group consisting of a phenyl group, a heterocyclic group, and a phenyl group substituted with an alkyl group, an alkoxy group, a halogen group, etc.

Another aspect of the present invention relates to a method for analyzing an ene compound, including reacting a triazolidinedione compound with a diene compound in the presence of an oxidizing agent to obtain the ene compound and analyzing the obtained ene compound, in which the triazolidinedione compound is represented by the following formula (7):

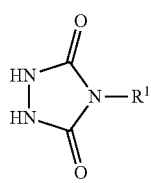

(7)

in which $R^1$ represents an organic group;

in which the diene compound is represented by the following formula (5):

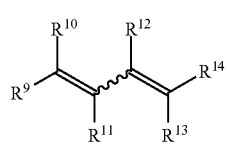

(5)

in which $R^9$, $R^{10}$, $R^{11}$, $R^{12}$, $R^{13}$, and $R^{14}$ each independently represent a group selected from the group consisting of an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^9$, $R^{10}$, $R^{11}$, $R^{12}$, $R^{13}$, and $R^{14}$ are optionally combined with one another; and in which the ene compound is represented by the following formula (6):

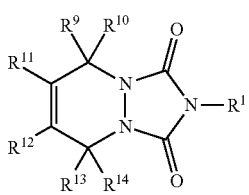

(6)

in which $R^1$ is as defined in the formula (7); and $R^9$, $R^{10}$, $R^{11}$, $R^{12}$, $R^{13}$ and $R^{14}$ are as defined in the formula (5).

The oxidizing agent may be a hypervalent iodine compound.

The oxidizing agent may be a hypervalent iodine compound represented by the following formula (8):

(8)

in which X and Y together represent an oxygen atom, or X and Y each independently represent a group selected from the group consisting of a hydroxy group, an alkoxy group, an acyloxy group, an acylamino group, a tosylamino group, a mesylamino group, a sulfonyloxy group, and a halogen group; and Ar represents a group selected from the group consisting of a phenyl group, a heterocyclic group, and a phenyl group substituted with an alkyl group, an alkoxy group, a halogen group, etc.

The analysis may be a method using high performance liquid chromatography.

The diene compound may be vitamin D3 or 25-hydroxyvitamin D3.

Effects of the Invention

The triazolinedione adduct of the present invention can be reacted while being reverted to a triazolinedione compound at the time of use and the triazolinedione adduct of the present invention can maintain its stability until the time of use. Therefore, it is possible to improve the stability of unstable triazolinedione compounds and to improve the handling property of the triazolinedione compounds.

Further, the triazolinedione adduct of the present invention easily returns to the triazolinedione compound by heating, and the triazolinedione compound reacts with a diene compound to generate an ene compound having high analytical sensitivity. Therefore, the triazolinedione adduct of the present invention is a very meaningful compound as a reagent for quantifying diene compounds.

Further, since the triazolinedione adduct of the present invention is an equivalent of a triazolinedione compound, the triazolinedione adduct can be used for producing various kinds of ene compounds, in addition to use as the above-described reagent for quantifying diene compounds.

Further, by using the triazolidinedione compound which is a precursor of the triazolinedione compound, feeding the triazolidinedione compound together with a diene, and performing an oxidation reaction while generating the triazolinedione compound in the system, it is possible to make the diene immediately react with the triazolinedione compound to obtain an ene compound. Thereby, it is possible to reduce the time during which an unstable triazolinedione compound exists and to obtain an ene compound derived from the triazolinedione compound in high yield.

PREFERRED MODE FOR CARRYING OUT THE INVENTION

Hereinafter, embodiments of the present invention will be described. The embodiments described below do not limit the present invention.

[Production Method (1) of Triazolinedione Adduct]

A first method of the present invention for producing the triazolinedione adduct is a method in which a triazolinedione compound represented by the following formula (4) and a fused ring compound having at least two aromatic rings are subjected to a Diels-Alder reaction to obtain the triazolinedione adduct.

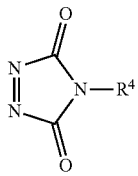

(4)

In the formula (4), $R^1$ represents an organic group.

[Triazolinedione Compound]

$R^1$ in the formula (4) preferably represents a group selected from the group consisting of a phenyl group, a nitrogen-containing heterocyclic group and an alkyl group which may have a substituent selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxyl group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

Still more preferably, $R^1$ in the formula (4) represents a group selected from the group consisting of a substituted phenyl group and substituted or unsubstituted methyl and ethyl groups. Examples of the substituent of the phenyl group include a dialkylamino group or a dialkylaminoalkyl group.

Further, $R^1$ in the formula (4) is particularly preferably a group selected from the group consisting of a methyl group, [2-(6,7-dimethoxy-4-methyl-3-oxo-3,4-dihydroquinoxalinyl)ethyl group, 4-nitrophenyl group, a ferrocenylmethyl group, 4-dimethylaminophenyl group, and 4-dimethylaminomethylphenyl group.

Therefore, as the triazolinedione compound used in the first method of the present invention for producing a triazolinedione adduct, a compound selected from the group consisting of 4-phenyl-1,2,4-triazoline-3,5-dione (PTAD), 4-methyl-1,2,4-triazoline-3,5-dione (MTAD), 4-[2-(6,7-dimethoxy-4-methyl-3-oxo-3,4-dihydroquinoxalinyl)ethyl]-1,2,4-triazoline-3,5-dione (DMEQTAD), 4-(4-nitrophenyl)-1,2,4-triazoline-3,5-dione (NPTAD), 4-ferrocenylmethyl-1,2,4-triazoline-3,5-dione (FMTAD), 4-(6-quinolyl)-1,2,4-triazoline-3,5-dione (QTAD), 4-(4'-diethylaminophenyl)-1,2,4-triazoline-3,5-dione (DEAPTAD), 4-(4'-dimethylaminophenyl)-1,2,4-triazoline-3,5-dione (DAPTAD), and 4-(4'-dimethylaminomethylphenyl)-1,2,4-triazoline-3,5-dione is particularly preferred. These compounds can be a Cookson-type derivatization reagent.

Further, $R^1$ in the formula (1) is most preferably a 4-dimethylaminophenyl group or a 4-dimethylaminomethylphenyl group. That is, the most preferred triazolinedione compound used in the first production method of the present invention for producing a triazolinedione adduct is 4-(4'-dimethylaminophenyl)-1,2,4-triazoline-3,5-dione (DAPTAD) or 4-(4'-dimethylaminomethylphenyl)-1,2,4-triazoline-3,5-dione.

[Fused Ring Compound Having at Least Two Aromatic Rings]

Examples of the fused ring compound having at least two aromatic rings include compounds having, for example, the following backbones. In the present invention, a part of hydrogen atoms included in these fused ring compounds having such a backbone may be substituted with a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group. Examples of the substituent which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like. Moreover, at least one selected from a cyclic alkyl group having 1 to 20 carbon atoms, a phenyl group, and a heterocyclic group may be fused with any of these fused ring compounds having such a backbone.

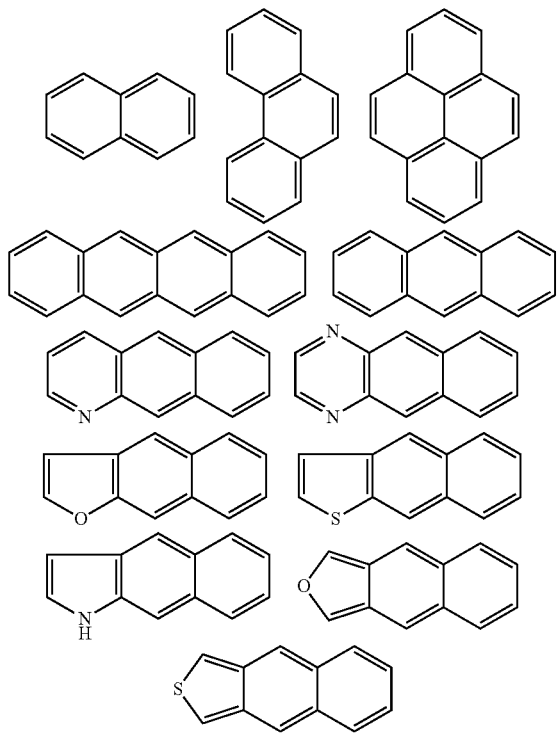

[Reaction Conditions]
(Reaction Solvent)

In the first production method of the triazolinedione adduct, the reaction solvent to be used when subjecting the triazolinedione compound represented by the formula (4) and the fused ring compound having at least two aromatic rings to Diels-Alder reaction is preferably at least one selected from the group consisting of esters, halogen-containing hydrocarbons, aromatic hydrocarbons, ketones, amides, alkylnitriles, dialkyl ethers, and ureas. Note that the diene compound to be subjected to the reaction per se may be used as the solvent.

The Diels-Alder reaction of the triazolinedione compound represented by the formula (4) with a fused ring compound having at least two aromatic rings is a reversible reaction. For this reason, in order to shift equilibrium of the reaction towards the production system, a solvent capable of crystallizing the product is preferred. In other words, in the production of the triazolinedione adduct, it is preferable to select a solvent in which the adduct is crystallized and in the reaction of the triazolinedione adduct and a diene compound, it is preferable to select a solvent in which the adduct is dissolved.

Examples of the solvent include aprotic solvents such as ethyl acetate, methyl acetate, butyl acetate, isopropyl acetate, tetrahydrofuran (THF), 2-methyltetrahydrofuran (2-methyl THF), 1,4-dioxane, t-butyl methyl ether, 1,2-dimethoxyethane, diglyme, acetone, diethyl ketone, methyl ethylketone, methylene chloride, chloroform, carbon tetrachloride, 1,2-dichloroethane, chlorobenzene, toluene, xylene, mesitylene, dimethylformamide (DMF), dimethyl acetamide (DMA), dimethyl sulfoxide (DMSO), N-methylpyrrolidone (NMP), 1,3-dimethyl-2-imidazolidinone (DMI), and the like. These may be used alone or as a mixed solvent.

Among these, at least one type selected from the group consisting of methylene chloride, chloroform, acetonitrile, 1,2-dimethoxyethane, toluene, chlorobenzene, and ethyl acetate is preferably used from the viewpoint of product crystallinity, yield, stability, safety, and price.

The amount of the solvent used in the reaction is preferably 5 to 1,000 volumes with respect to 1 part by mass of the reaction substrate.

(Reaction Temperature)

The temperature for the reaction of the triazolinedione compound represented by the formula (4) with the fused ring compound having at least two aromatic rings is preferably in the range of −10° C. to 60° C., and more preferably in the range of 0° C. to 40° C.

(Reaction Time)

The reaction time during which the triazolinedione compound represented by the formula (4) is reacted with the fused ring compound having at least two aromatic rings is preferably 10 minutes to 48 hours, and more preferably in the range of 1 to 10 hours.

(Feed Amount)

In the reaction of the triazolinedione compound represented by the formula (4) with the fused ring compound having at least two aromatic rings, the used amount of the fused ring compound is preferably in the range of 1.0 to 10,000 equivalents with respect to 1 equivalent of the triazolinedione compound.

(Others)

For the purpose of removing water generated by the reaction, a dehydrating agent such as a molecular sieve may be added to the reaction solvent to perform the reaction.

[Crystallization Conditions]

The first method for producing a triazolinedione adduct includes reacting a triazolinedione compound represented by the formula (4) with a fused ring compound having at least two aromatic rings to obtain a triazolinedione adduct. The obtained triazolinedione adduct may be crystallized and obtained as a solid.

(Crystallization Solvent)

Examples of the solvent for crystallizing the obtained triazolinedione adduct include aprotic solvents such as methylene chloride, chloroform, dimethylformamide, dimethylacetamide, dimethyl sulfoxide, acetonitrile, 1,2-dimethoxyethane, toluene, xylene, chlorobenzene, mesitylene, ethyl acetate, hexane, heptane, pentane, cyclopentane, cyclohexane, isohexane, isooctane, decane, and the like, and protic solvents such as water, methanol, ethanol, 2-propanol, 2-butanol, and butanol. These may be used alone or as a mixed solvent.

The amount of the solvent used for crystallization is preferably 5 to 1,000 volumes with respect to 1 part by mass of the obtained triazolinedione adduct.

(Crystallization Temperature)

The temperature at which the triazolinedione adduct is crystallized is preferably in the range of −10 to 40° C.

(Crystallization Time)

The time duration for crystallizing the triazolinedione adduct is preferably in the range from 30 minutes to 24 hours, and more preferably from 1 to 10 hours.

[Purification Step]

The first method for producing a triazolinedione adduct may further comprise a purification step of purifying the resulting triazolinedione adduct. The purification method is not particularly limited, and examples thereof include silica gel column chromatography. As the developing solvent, a mixed solvent of a low polarity solvent and a high polarity solvent can be used. Examples of the low polarity solvent include hexane, heptane, etc. and examples of the high polarity solvent include ethyl acetate, tetrahydrofuran, etc.
<Production Method (2) of Triazolinedione Adduct>

The second method of the present invention for producing a triazolinedione adduct is a method including reacting a triazolidinedione compound represented by the following formula (7) with a fused ring compound having at least two aromatic rings in the presence of an oxidizing agent to obtain the triazolinedione adduct.

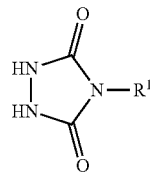

(7)

In the formula (7), $R^1$ represents an organic group.

[Triazolidinedione Compound]

The compound represented by the formula (7), which serves as a starting material in the second method for producing a triazolinedione adduct, is a triazolidinedione compound that includes a urazole group, i.e., a triazolidinedione compound which includes a 1,2,4-triazolidine-3,5-dione group.

$R^1$ in the formula (7) preferably represents a group selected from the group consisting of a phenyl group, a nitrogen-containing heterocyclic group and an alkyl group which may have a substituent selected from the group consisting of a disubstituted amino group, a disubstituted aminoalkyl group, a nitro group, an azide group, an alkoxy group, a halogen group, an alkylthio group, a sulfonyl group, a phosphoric acid group, a carboxyl group, an ester group, a nitrile group, an amide group, a ferrocenyl group, and a substituted quinoxalinyl group, in which the two substituents included in the disubstituted amino group or the disubstituted aminoalkyl group are identical to or different from each other and are each selected from the group consisting of an alkyl group, an aralkyl group, and an aryl group, and in which the alkyl group, the aralkyl group and the aryl group optionally contain an oxygen atom or a nitrogen atom.

Still more preferably, $R^1$ in the formula (7) represents a group selected from the group consisting of substituted or unsubstituted phenyl, methyl and ethyl groups.

$R^1$ in the formula (7) is particularly preferably a group selected from the group consisting of a phenyl group, a methyl group, [2-(6,7-dimethoxy-4-methyl-3-oxo-3,4-dihydroquinoxalinyl) ethyl group, 4-nitrophenyl group, a ferrocenylmethyl group, 6-quinolyl group, 4-diethylaminophenyl group, 4-dimethylaminophenyl group and 4-dimethylaminomethylphenyl group.

Among them, 4-(4'-dimethylaminophenyl)-1,2,4-triazolidine-3,5-dione (DMU) or 4-(4'-dimethylaminomethylphenyl)-1,2,4-triazolidine-3,5-dione is the most preferable, as the triazolidinedione compound used in the second method of the present invention for producing a triazolinedione adduct.

[Oxidizing Agent]

The oxidizing agent used in the second method of the present invention for producing a triazolinedione adduct is not particularly limited as long as the oxidizing agent enables the triazolidinedione compound represented by the formula (7) to react with a fused ring compound having at least two aromatic rings and produce a triazolinedione adduct, but the oxidizing agent is preferably a hypervalent iodine compound. The hypervalent iodine compound enables a smooth conversion from a triazolidinedione compound to a triazolinedione adduct.

Moreover, among hypervalent iodine compounds, a compound represented by the following formula (8) is more preferred.

(8)

In the formula (8), X and Y together represent an oxygen atom, or X and Y each independently represent a group selected from the group consisting of a hydroxy group, an alkoxy group, an acyloxy group, an acylamino group, a tosylamino group, a mesylamino group, a sulfonyloxy group, and a halogen group; and Ar represents a group selected from the group consisting of a phenyl group, a heterocyclic group, and a phenyl group substituted with an alkyl group, an alkoxy group, a halogen group, etc.

Examples of the compound represented by the formula (8) include idosobenzene, iodobenzene diacetate, iodobenzene triflate, iodobenzene tosylate, iodobenzene mesylate, iodobenzene dichloride and iodobenzene dibromide, etc. Among these, iodosobenzene or iodobenzene diacetate is especially preferable from the viewpoint of yield, stability and price.

The used amount of an oxidizing agent is preferably set to 1 to 10 molar equivalents, more preferably 1 to 5 molar equivalents, with respect to the triazolidinedione compound serving as a starting material. A range of 1 to 5 molar equivalents is preferred, because the oxidizing agent which remains after the reaction and decomposition products thereof can be easily removed.

[Fused Ring Compound Having at Least Two Aromatic Rings]

The fused ring compound having at least two aromatic rings which can be used in the second method for producing a triazolinedione adduct is the same as those used in the first method for producing the triazolinedione adduct described above.

[Reaction Conditions]

(Reaction Solvent)

In the second method for producing a triazolinedione adduct, a solvent used in reacting the triazolidinedione compound represented by the formula (7) with the fused ring compound having at least two aromatic rings in the presence of an oxidizing agent is the same as the solvent used in the first method for producing the triazolinedione adduct described above. The used amount thereof is the same as in the first method for producing a triazolinedione adduct described above.

(Reaction Temperature)

The temperature at which the triazolidinedione compound represented by the formula (7) is reacted with a fused ring compound having at least two aromatic rings is the same as that of the first method for producing the triazolinedione adduct.

(Reaction Time)

In addition, the reaction time during which the triazolidinedione compound represented by the formula (7) is reacted with a fused ring compound having at least two aromatic rings is the same as that in the first method for producing the triazolinedione adduct.
(Feed Amount)

In the reaction of the triazolidinedione compound represented by the formula (7) with a fused ring compound having at least two aromatic rings, the amount of the fused ring compound used is the same as in the first method for producing the triazolinedione adduct described above.
(Others)

In the same manner as in the first method for producing the triazolinedione adduct described above, a dehydrating agent such as a molecular sieve may be added to the reaction solvent for the purpose of removing water generated by the reaction to perform the reaction.
[Crystallization Conditions]

It is also possible to crystallize the obtained triazolinedione adduct and obtain the triazolinedione as a solid in the second method for producing a triazolinedione adduct, as in the first method for producing the triazolinedione adduct. The type of solvent used for crystallization, the amount used, the crystallization temperature, and the crystallization time are the same as those of the first method for producing the triazolinedione adduct.
[Purification Step]

The second production method of the triazolinedione adduct may further comprise a purification step of purifying the resulting triazolinedione adduct. The purification method is not particularly limited, and may be the same as in the purification method in the first method for producing the triazolinedione adduct described above.
<Triazolinedione Adduct>

The triazolinedione adduct of the present invention is the triazolinedione adduct represented by the following formula (1).

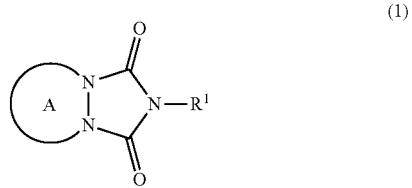

(1)

In the formula (1), $R^1$ represents an organic group and A represents a fused ring having three or more rings including at least one aromatic ring.

The triazolinedione adduct of the present invention undergoes a reverse reaction (retro-Diels-Alder reaction) to a fused ring compound having at least two aromatic rings and a triazolinedione compound represented by the formula (4), which are starting materials, by heating. Therefore, the triazolinedione adduct of the present invention can be reacted while being reverted to the triazolinedione compound, and thus the triazolinedione adduct of the present invention remains in a stable state until the time of use.

In the reverse reaction, the temperature is in the range of −78 to 200° C., and the reaction time is in the range of 0.01 to 48 hrs. Examples of the most suitable solvents for producing the triazolinedione compound from the triazolinedione adduct by the retro-Diels-Alder reaction include acetonitrile, ethyl acetate, dioxane, acetone, and the like. In the retro-Diels-Alder reaction, when the concentration of the triazolinedione adduct is higher, the triazolinedione compound can be produced at a higher concentration, so that the concentration of the triazolinedione adduct is preferably 1 mmol/L or more, more preferably 5 mmol/L or more, and particularly preferably 10 mmol/L or more. Additionally, the retro-Diels-Alder reaction is an endothermic reaction, so that higher temperatures are favorable for the formation of the triazolinedione compound.

The triazolinedione adduct of the present invention represented by the formula (1) can be obtained by the method of the present invention for producing a triazolinedione adduct.

$R^1$ in the formula (1) is the same as $R^1$ in the triazolinedione compound represented by the formula (4), which is used in the method of the present invention for producing a triazolinedione adduct.

Examples of the triazolinedione adduct of the present invention include those represented by the following formula (2).

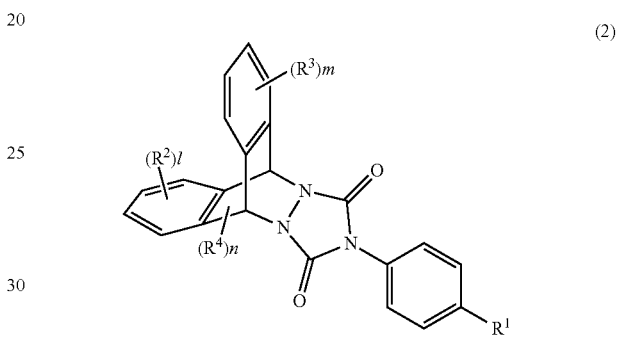

(2)

In the formula (2), $R^1$ represents an organic group; $R^2$, $R^3$, and $R^4$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and n is an integer of 0 to 2.

In the above-mentioned $R^2$, $R^3$, and $R^4$, examples of the substituents which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like.

Further, examples of the triazolinedione adduct of the present invention include those represented by the following formula (3).

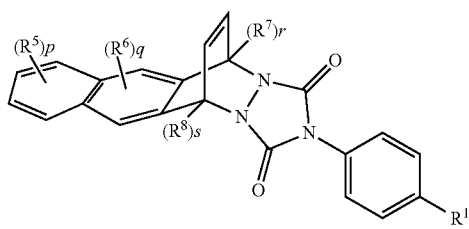

(3)

In the formula (3), $R^1$ represents an organic group; $R^5$, $R^6$, $R^7$, and $R^8$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; p is an integer of 0 to 4; q is an integer of 0 to 2; and r and s are integers of 0 or 1.

In the above-mentioned $R^5$, $R^6$, $R^7$, and $R^8$, examples of the substituents which may be included in the substituent selected from the group consisting of an alkyl group, an aralkyl group, an alkenyl group, a phenyl group, an acyl group, an amino group, and a heterocyclic group include: alkyl groups such as a methyl group, an ethyl group, a propyl group, a butyl group, an isobutyl group, a t-butyl group, a chloromethyl group, a 2-chloroethyl group, a 3-chloropropyl group, a 2-chloropropyl group, a 1-chloropropyl group, a bromomethyl group, a 2-bromoethyl group, a 3-bromopropyl group, a 2-bromopropyl group, and 1-bromopropyl group; aralkyl groups such as a benzyl group, a phenethyl group, a 3-phenylpropyl group, a 4-methylbenzyl group, and a 4-methylphenethyl group; alkenyl groups such as a vinyl group, an allyl group, a propenyl group, a cyclopropenyl group, a 2-chlorovinyl group, a 3-chloroallyl group, a cinnamyl group, and a styryl group; phenyl groups such as a phenyl group, a tolyl group, a xylyl group, and a trityl group; acyl groups such as a formyl group, an acetyl group, a propionyl group, a benzoyl group, an acryloyl group, and a methacryloyl group; halogen groups such as a chloro group, a bromo group, a fluoro group, and an iodo group; amino groups such as an amino group, a methylamino group, a dimethylamino group, an ethylamino group, and a diethylamino group; a nitro group; heterocyclic groups such as a quinolyl group, a pyridyl group, a pyrrolidyl group, a pyrrolyl group, a furyl group, a thienyl group, and a lutidyl group; and the like.

<Production Method (1) of Ene Compound>

The first method of the present invention for producing an ene compound comprises reacting the triazolinedione adduct represented by the formula (1) and the diene compound represented by the following formula (5) to obtain the ene compound represented by the following formula (6).

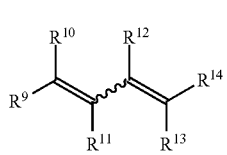

(5)

In the formula (5), $R^9$, $R^{10}$, $R^{11}$, $R^{12}$, $R^{13}$, and $R^{14}$ each independently represent a group selected from the group consisting of an alkyl group having 1 to 100 carbon atoms, an aralkyl group, a phenyl group, and a heterocyclic group, in which the alkyl group, the aralkyl group, the phenyl group, and the heterocyclic group optionally contain an atom selected from the group consisting of an oxygen atom, a nitrogen atom, a sulfur atom, and a phosphorus atom, and in which at least two of $R^9$, $R^{10}$, $R^{11}$, $R^{12}$, $R^{13}$, and $R^{14}$ are optionally combined with one another.

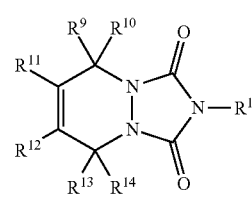

(6)

In the formula (6), $R^1$ is as defined in the formula (1); and $R^9$, $R^{10}$, $R^{11}$, $R^{12}$, $R^{13}$ and $R^{14}$ are as defined in the formula (5).

$R^9$, $R^{10}$, $R^{11}$, $R^{12}$, $R^{13}$, and $R^{14}$ in the formulas (5) and (6) are preferably anthracene and naphthalene each having the above substituents and more preferably anthracene having the above substituents, from the viewpoint of the generation rates of the triazolinedione adduct, crystallinity, moderate thermal stability, safety, and price.

[Diene Compound]

From the viewpoint of usefulness, yield, safety, and price of the product, the diene compound represented by the formula (5) is preferably a polymer or a compound selected from the group consisting of natural products of a small molecule, bioactive compounds such as a medicine, functional materials, and intermediates thereof. Examples of such a compound include an anthracene derivative having a substituent, a quinoline derivative having a substituent, a vitamin, an amino acid, and a steroid.

[Reaction Conditions]

(Reaction Solvent)

As a solvent which can be used in reacting the triazolinedione adduct represented by the formula (1) with the diene compound represented by the formula (5), solvents which are similar to the solvents used in reacting the triazolinedione compound represented by the formula (4) with the fused ring compound having at least two aromatic rings in the first method of the present invention for producing a triazolinedione adduct can be used.

As described above, a Diels-Alder reaction of the triazolinedione compound represented by the formula (4) with the fused ring compound having at least two aromatic rings is a reversible reaction. For this reason, in order to shift equilibrium of the reaction towards the production system, a solvent capable of crystallizing the product is preferred. In other words, it is preferable to select a solvent in which the adduct is crystallized in the production of the triazolinedione adduct described above and it is preferable to select a solvent in which the adduct is dissolved in the reaction of the triazolinedione adduct represented by the formula (1) with the diene compound represented by the formula (5) to obtain an ene compound.

In the first method of the present invention for producing an ene compound, it is preferable to use at least one type selected from the group consisting of chloroform, acetonitrile, 1,2-dimethoxyethane, ethyl acetate, and dimethyl sulfoxide (DMSO), from the viewpoint of solubility, boiling point, yield, safety, and price.

The amount of the solvent used in the reaction is preferably 5 to 1,000 volumes with respect to 1 part by mass of the reaction substrate.

(Reaction Temperature)

The temperature at which the triazolinedione adduct represented by the formula (1) is reacted with the diene compound represented by the formula (5) is preferably in the range of 20 to 350° C., and more preferably in the range of 40 to 200° C.

(Reaction Time)

The reaction time during which the triazolinedione adduct represented by the formula (1) is reacted with the diene compound represented by the formula (5) is preferably 1 minute to 12 hours, and more preferably in the range of 1 minute to 8 hours.

(Feed Amount)

In the reaction of the triazolinedione adduct represented by the formula (1) with the diene compound represented by the formula (5), the used amount of the diene compound represented by the formula (5) is preferably in the range of 1 to 10 equivalents of the diene compound represented by the formula (5), more preferably in the range of 1 to 5 equivalents, with respect to 1 equivalent of the triazolinedione adduct.

<Analysis Method (1) of Ene Compound>

A first method of the present invention for analyzing an ene compound comprises reacting the diene compound represented by the formula (5) with the triazolinedione adduct represented by the formula (1) to obtain the ene compound represented by the formula (6), and analyzing the obtained ene compound.

(Analysis Method)

The analysis method is not particularly limited, but a method using mass spectrometry or high performance liquid chromatography is preferred from the viewpoint of sensitivity, accuracy, and ease of measurement.

(Diene Compound)

The diene compound applicable to the first analysis method of the present invention of an ene compound is not particularly limited, but it is preferable that the triazolinedione adduct of the present invention, which is represented by the formula (1), is vitamin D3 or 25-hydroxyvitamin D3 because the triazolinedione adduct can act as a Cookson type derivatization reagent.

<Production Method (2) of Ene Compound>

A second method of the present invention for producing an ene compound comprises reacting the triazolidinedione compound represented by the formula (7) and the diene compound represented by the formula (5) in the presence of an oxidizing agent to obtain the ene compound represented by the formula (6).

[Reaction Formula]

Typical reaction formulas for the second method of the present invention for producing an ene compound are shown below. Note that the following exemplifies an example of the present invention, and the present invention is not limited to the following.

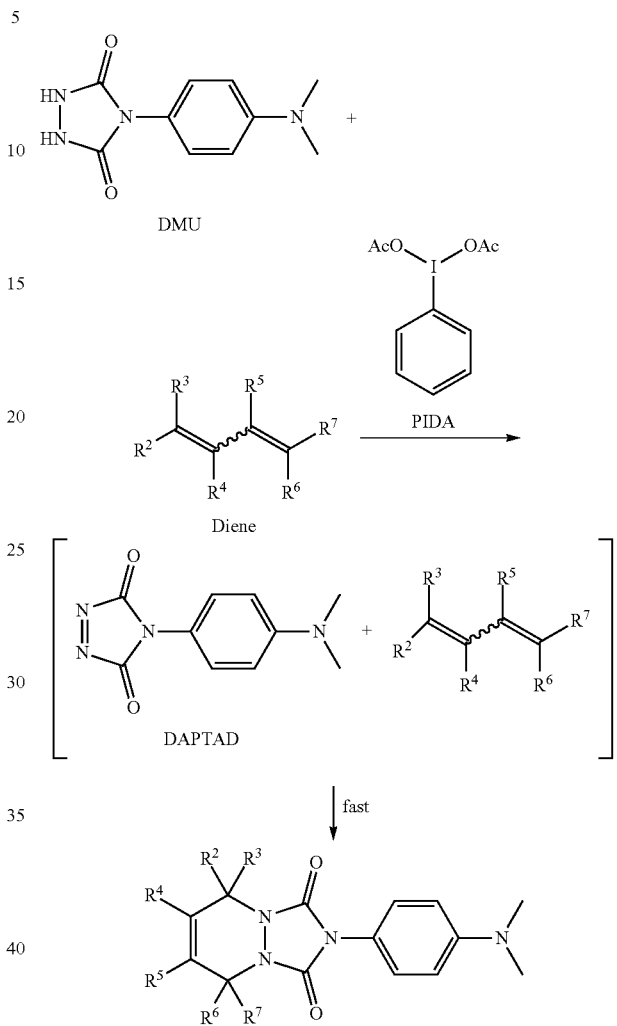

[Triazolidinedione Compound]

In the second method of the present invention for producing an ene compound, the compound of the formula (7) serving as a starting material is the same as the compound serving as a starting material in the second method of the present invention for producing a triazolinedione adduct.

Therefore, as the triazolinedione compound generated in the reaction system by the oxidation reaction in the second method of the present invention for producing an ene compound, a compound selected from the group consisting of 4-phenyl-1,2,4-triazoline-3,5-dione (PTAD), 4-methyl-1,2,4-triazoline-3,5-dione (MTAD), 4-[2-(6,7-dimethoxy-4-methyl-3-oxo-3,4-dihydroquinoxalinyl)ethyl]-1,2,4-triazoline-3,5-dione (DMEQTAD), 4-(4-nitrophenyl)-1,2,4-triazoline-3,5-dione (NPTAD), 4-ferrocenylmethyl-1,2,4-triazoline-3,5-dione (FMTAD), 4-(6-quinolyl)-1,2,4-triazoline-3,5-dione (QTAD), 4-(4'-diethylaminophenyl)-1,2,4-triazoline-3,5-dione (DEAPTAD), 4-(4'-dimethylaminophenyl)-1,2,4-triazoline-3,5-dione (DAPTAD), and 4-(4'-dimethylaminomethylphenyl)-1,2,4-triazoline-3,5-dione is particularly preferred.

21

[Diene Compound]

The diene compound represented by the formula (5) is the same as the compound used in the first method of the present invention for producing an ene compound.

[Oxidizing Agent]

The oxidizing agent used in the second method of the present invention for producing an ene compound is not particularly limited as long as the oxidizing agent enables the triazolidinedione compound represented by the formula (7) and the diene compound represented by the formula (5) to react with each other and produce the ene compound represented by the formula (6), but the oxidizing agent is preferably the same as the compound used in the second method of the present invention for producing a triazolinedione adduct. In other words, the oxidizing agent is preferably a hypervalent iodine compound, and further, among hypervalent iodine compounds, the oxidizing agent is more preferably a compound represented by the formula (4).

The used amount of oxidizing agent is also the same as the used amount in the first method of the present invention for producing an ene compound, and is preferably set to 1 to 10 molar equivalents, more preferably 1 to 5 molar equivalents, with respect to the triazolidinedione compound serving as a starting material.

[Reaction Condition]

(Reaction Solvent)

As a solvent used in the second method of the present invention for producing an ene compound, the same solvent as the solvent used in reacting the triazolinedione compound represented by the formula (4) with the fused ring compound including at least two aromatic rings in the above-described first method for producing a triazolinedione adduct can be used.

Among them, from the viewpoint of accelerating the oxidation reaction, stability against the oxidation reaction, and stability of the ene compound to be generated, at least one type selected from the group consisting of methylene chloride, acetonitrile, 1,2-dimethoxyethane, tetrahydrofuran (THF), toluene, ethyl acetate, chlorobenzene, and dimethyl sulfoxide (DMSO) is preferably used.

The amount of the solvent used in the reaction is preferably 1 to 5,000 volumes per 1 part by mass of the reaction substrate.

(Reaction Temperature)

The temperature at which the triazolidinedione compound represented by the formula (7) is reacted with the diene compound represented by the formula (5) is preferably in the range of −10 to 60° C., and more preferably in the range of 10 to 40° C.

(Reaction Time)

The reaction time during which the triazolidinedione compound represented by the formula (7) is reacted with the diene compound represented by the formula (5) is preferably set to the range of 30 minutes to 48 hours, and more preferably in the range of 1 to 10 hours.

(Feed Amount)

In the reaction of the triazolidinedione compound represented by the formula (7) with the diene compound represented by the formula (5), the used amount of the diene compound represented by the formula (5) is preferably in the range of 1 to 10 molar equivalents of the diene compound, more preferably in the range of 1 to 5 molar equivalents, with respect to 1 equivalent of the triazolidinedione compound, in the same manner as in the first method for producing a triazolinedione adduct.

22

EXAMPLES

Subsequently, the Examples of the present invention will be described, but the present invention is not limited to these Examples.

Example 1

[Synthesis of Anthracene Adduct (DAP-A)]

In a light-shielding vessel, 81 mg (0.45 mmol) of anthracene was dissolved in 10 mL of dry acetonitrile to obtain an acetonitrile solution containing anthracene dissolved. Further, 98.2 mg (0.45 mmol) of 4-(4'-dimethylaminophenyl)-1,2,4-triazoline-3,5-dione (DAPTAD) was added, and the mixture was stirred at 20° C. for 4 hours to obtain a suspension.

The resultant suspension was filtered, and the solid was washed with hexane and dried to obtain a triazolinedione adduct. The resultant triazolinedione adduct was 5,10-dihydro-2-(4-dimethylaminophenyl)-5,10-[1',2']-benzeno-1H-[1,2,4]triazolo[1,2-b]phthalazine-1,3(2H)-dione (DAP-A), and the yield was 75 mg, 42%.

[Reaction Scheme]

The reaction scheme carried out in Example 1 is shown below.

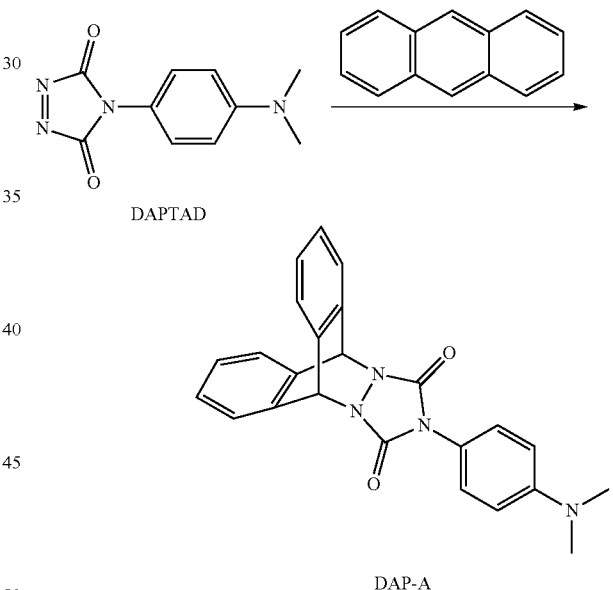

[Evaluation of Physical Properties]

Various analyses were carried out on the resultant DAP-A. The results are shown below.

Mp: 217 to 218° C.

IR (KBr): 1780, 1717 cm$^{-1}$ $^1$H-NMR (CDCl$_3$): δ 7.20-7.75 (m, 8H), 6.50-7.15 (m, 4H), 6.25 (s, 2H), 3.00 (s, 6H)

Example 2

[Synthesis of 9-Methylanthracene Adduct (DAP-MA)]

In a light-shielding vessel, 87 mg (0.45 mmol) of 9-methylanthracene was dissolved in 5 mL of dry acetonitrile to obtain an acetonitrile solution containing 9-methylanthracene dissolved. Further, 98.2 mg (0.45 mmol) of 4-(4'-dimethylaminophenyl)-1,2,4-triazoline-3,5-dione (DAPTAD) was added, and the mixture was stirred at 20° C. for 2 hours to obtain a suspension.

The resultant suspension was filtered, and the solid was washed with hexane and dried to obtain a triazolinedione adduct. The resultant triazolinedione adduct was 5,10-dihydro-2-(4-dimethylaminophenyl)-5-methyl-5,10-[1',2']-benzeno-1H-[1,2,4]triazolo[1,2-b]phthalazine-1,3(2H)-dione (DAP-MA), and the yield was 95 mg, 51.4%.

[Reaction Scheme]

The reaction scheme carried out in Example 2 is shown below.

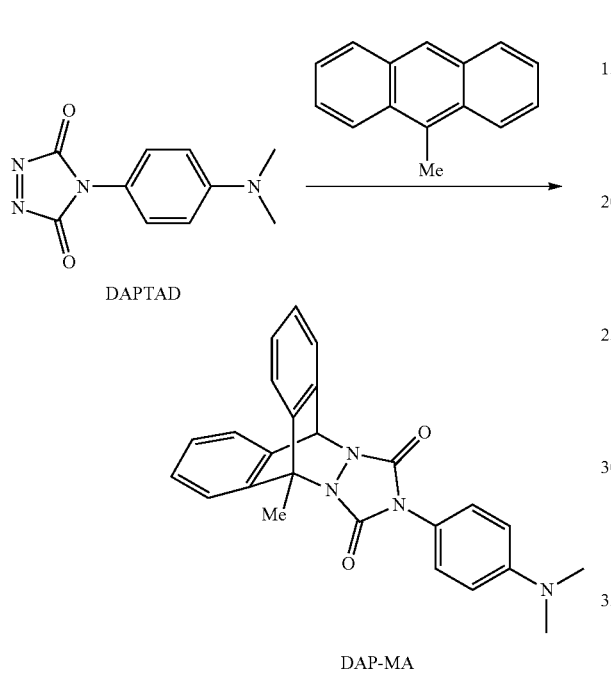

DAP-MA

[Evaluation of Physical Properties]

Various analyses were carried out on the resultant DAP-MA. The results are shown below.

Mp: >218° C.
IR (KBr): 1765, 1708 cm$^{-1}$
$^1$H-NMR (CDCl$_3$): δ 7.10-7.75 (m, 8H), 6.50-7.20 (m, 4H), 6.25 (s, 1H), 3.00 (s, 3H), 2.70 (s, 3H)

Example 3

[Synthesis of 9-Phenylanthracene Adduct (DAP-PA)]

In a light-shielding vessel, 0.50 g (1.97 mmol) of 9-phenylanthracene was dissolved in 50 mL of dry methylene chloride to obtain a methylene chloride solution containing 9-phenylanthracene dissolved. Further, 50 mg of molecular sieves 3 Å (MS-3 Å) and 0.426 g (1.95 mmol) of 4-(4'-dimethylaminophenyl)-1,2,4-triazoline-3,5-dione (DAPTAD) were added, and the mixture was stirred at 20° C. for 2 hours, to obtain a reaction solution.

The resultant reaction solution was filtered, then 100 mL of hexane was added to the filtrate, and the mixture was stirred for 2 hours in an ice bath, followed by filtration to filter out insolubles. To the resultant filtrate 200 mL of hexane was added, and the mixture was stirred for 30 minutes at room temperature. Precipitated crystals were filtered, and dried under reduced pressure to give a triazolinedione adduct. The resultant triazolinedione adduct was 5,10-dihydro-2-(4-dimethylaminophenyl)-5-phenyl-5,10[1', 2']-benzeno-1H-[1,2,4]triazolo[1,2-b]phthalazine-1,3(2H)-dione (DAP-PA), and the yield was 0.54 g, 58.6%.

[Reaction Scheme]

The reaction scheme carried out in Example 3 is shown below.

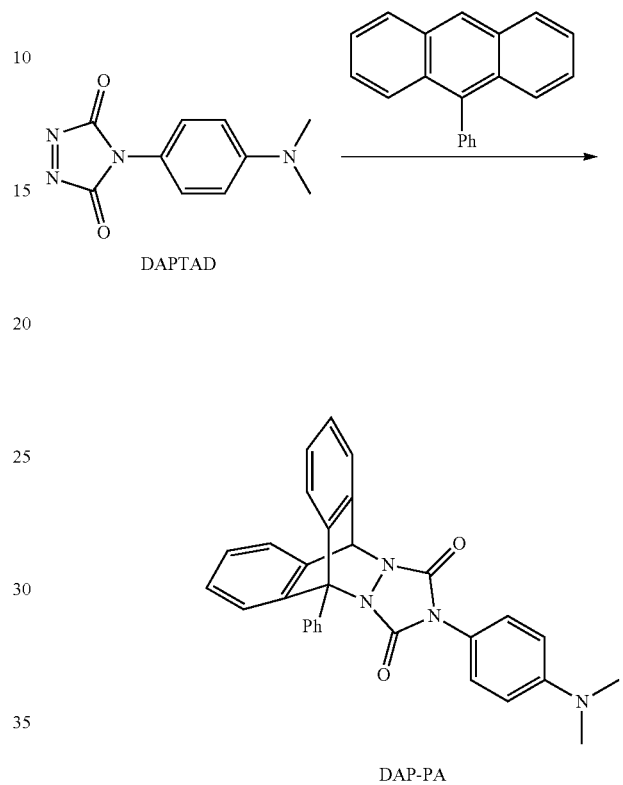

DAP-PA

[Evaluation of Physical Properties]

Various analyses were carried out on the resultant DAP-PA. The results are shown below.

Mp: >200° C.
IR (KBr): 1774, 1714 cm$^{-1}$
$^1$H-NMR (CDCl$_3$): δ 6.25-8.10 (m, 17H), 2.80 (s, 6H)

Example 4

[Synthesis of 9,10-Diphenylanthracene Adduct (DAP-DPA)]

In a light-shielding vessel, 0.75 g (2.27 mmol) of 9,10-diphenylanthracene was dissolved in 75 mL of toluene to obtain a toluene solution containing 9,10-diphenylanthracene dissolved. Further, 0.495 g (2.27 mmol) of 4-(4'-dimethylaminophenyl)-1,2,4-triazoline-3,5-dione (DAPTAD) was added, and the mixture was stirred for 3 hours at room temperature, to obtain a reaction solution.

The resultant reaction solution was filtered, then the filtrate was purified by a silica gel column chromatography (toluene to toluene/ethyl acetate=10/1), to give a triazolinedione adduct. The resultant triazolinedione adduct was 12-dihydro-2-(4-dimethylaminophenyl)-6,11-diphenyl-5, 12-etheno-1H-benzo[g][1,2,4]triazolo[1,2-b]phthalazine-1, 3(2H)-dione (DAP-DPA), and the yield was 43 mg, 3.4%.

[Reaction Scheme]

The reaction scheme executed in Example 4 is shown below.

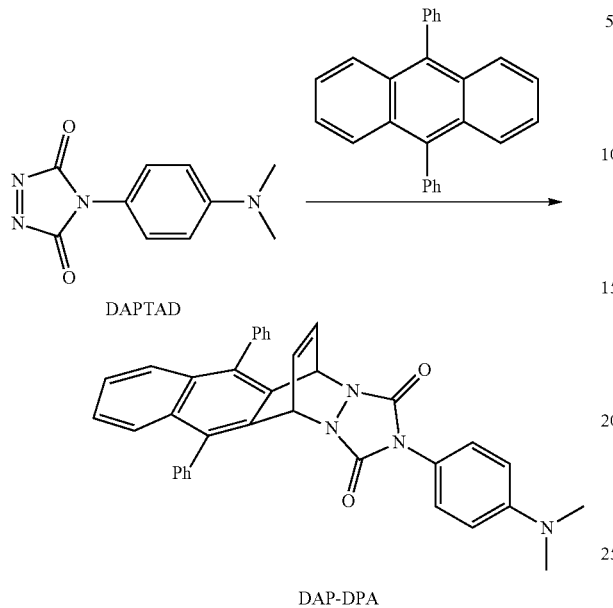

DAPTAD

DAP-DPA

[Evaluation of Physical Properties]

Various analyses were carried out on the resultant DAP-DPA. The results are shown below.

Mp: >200° C.

IR (KBr): 1764, 1705 cm$^{-1}$ $^{1}$H-NMR (DMSO-$d_6$): δ 7.30-8.00 (m, 16H), 6.70-7.30 (m, 4H), 5.50-5.80 (m, 2H), 2.90 (s, 6H)

Example 5

[Reaction of 9-Methylanthracene Adduct (DAP-MA) and TTB (Synthesis of Ene Compound)]

10 mg (0.024 mmol) of 9-methylanthracene adduct (DAP-MA) and 10 mg (0.048 mmol) of trans,trans-diphenylbutadiene (TTB) were dissolved in 0.2 g of dimethylsulfoxide (DMSO) to obtain a dimethylsufoxide solution.

Upon stirring the obtained DMSO solution at 120° C. for 3 hours, a TTB-DAPTAD adduct, which is an ene compound, i.e., cis-2-(4-dimethylaminophenyl)-5,8-diphenyl-1H-[1,2,4]triazolo[1,2-a]pyridazine-1,3(2H)-dione(DAP-TAC) was generated. With respect to a conversion ratio, high performance liquid chromatography (HPLC) analysis was performed under the following conditions to find the conversion ratio as being 60%.

(Analysis Conditions)
  Sample concentration: 0.05%
  Injection volume: 1.0 μL
  Wavelength: 254 nm
  Flow rate: 1.0 mL/min.
  Mobile phase: 0 to 15 min. (CH$_3$CN:water=50:50 to CH$_3$CN:water=100:0)
  15 to 20 min. (CH$_3$CN:water=100:0)
  Column temperature: 30° C.
  Packing material: X Bridge C18 5 μm (4.6×150)
  Retention time: DAPTAC: 7.2 min.
  TTB: 11.4 min.

The reaction solution was concentrated and the concentrated residue was purified by a silica gel column chromatography (eluting solvent: ethyl acetate) to obtain a pure product of DAPTAC.

[Reaction Scheme]

The reaction scheme carried out in Example 5 is shown below.

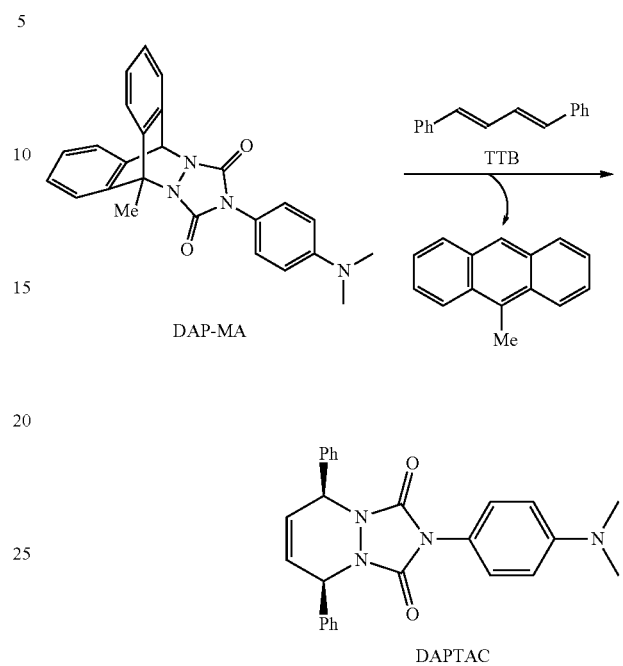

DAP-MA

DAPTAC

[Evaluation of Physical Properties]

Various analyses were carried out on the resultant DAP-TAC. The results are shown below.

Mp: 174 to 177° C.

IR (KBr): 1772, 1700 cm$^{-1}$ $^{1}$H-NMR (CDCl$_3$): δ 7.10-7.75 (m, 12H), 6.50-6.85 (m, 2H), 6.00 (s, 2H), 5.51 (s, 2H), 2.90 (s, 6H)

Example 6

[Reaction of 9-Phenylanthracene Adduct (DAP-PA) and Vitamin D3 (Synthesis of Ene Compound)]

50 mg (0.106 mmol) of 9-phenylanthracene adduct (DAP-PA) and 40 mg (0.103 mmol) of vitamin D3 were dissolved in 5 mL of 1,2-dimethoxyethane (DME) to obtain a DME solution. The obtained DME solution was stirred at 70° C. for 5 hours to obtain a reaction solution.

The obtained reaction solution was analyzed using a high performance liquid chromatography (HPLC) under the same conditions as in Example 5, and as result, it was found that 51.4 mg (yield 82.7%) of a vitamin D3 adduct, an ene compound, that is, (5S,7S)-2-[4-(dimethylamino)phenyl]-5-[(E)-[(1R,3aS,7aR)-1-[(1R)-1,5-dimethylhexyl]octahydro-7a-methyl-4H-indene-4-ylidene]methyl]-5,6,7,8,9,10-hexahydro-7-hydroxy-1H-[1,2,4]triazolo[1,2-b]phthaldine-1,3(2H)-dione was contained. Further, 2.44 mg of vitamin D3 was contained (recovery rate: 6.1%).

The obtained reaction solution was concentrated under reduced pressure and the concentrated residue was purified by a silica gel column chromatography (eluting solvent: hexane/ethyl acetate=4/1→2/1) to isolate the vitamin D3 adduct.

[Reaction Scheme]
The reaction scheme carried out in Example 6 is shown below.

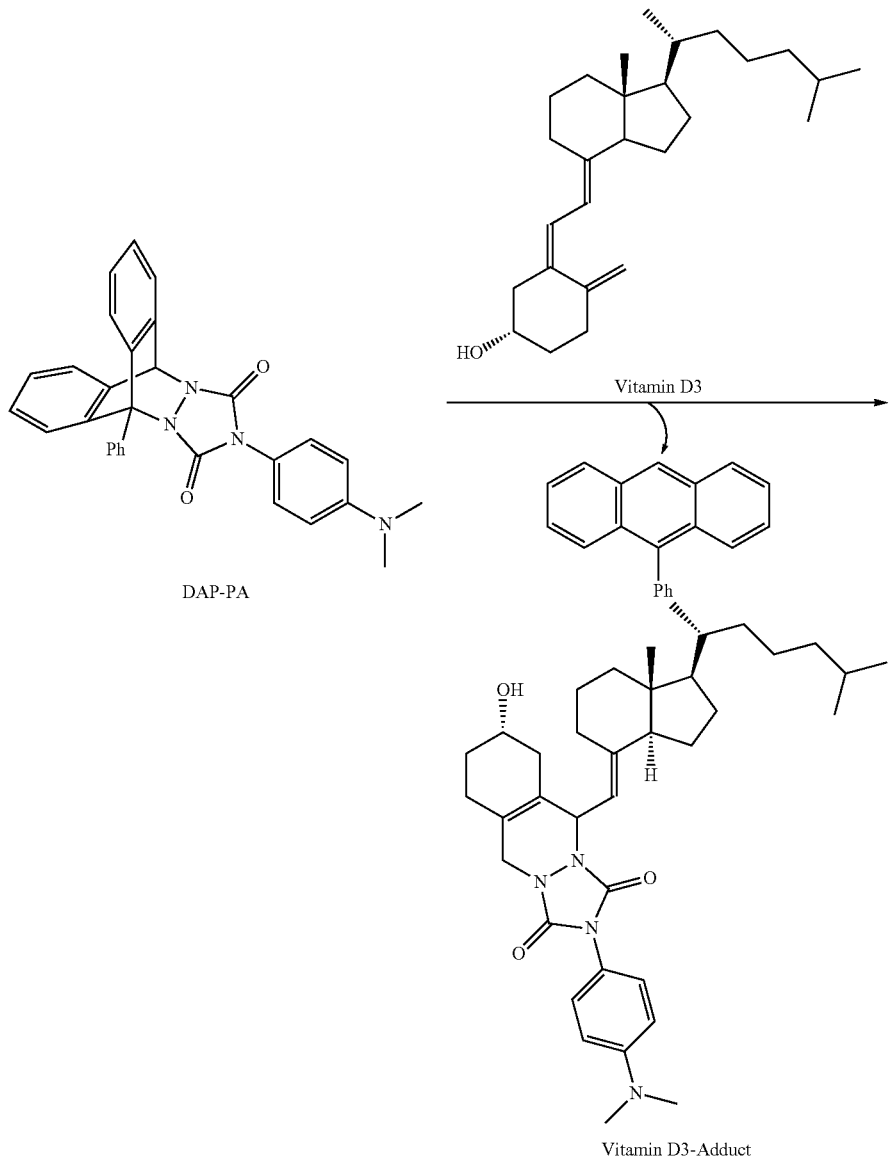

[Evaluation of Physical Properties]
Various analyses were carried out on the resultant vitamin D3. The results are shown below.
Mp: 125 to 129° C.
IR (KBr): 1762, 1697 cm$^{-1}$
$^1$H-NMR (CDCl$_3$): δ 7.25 (d, J=15 Hz, 2H), 6.75 (d, J=15 Hz, 2H), 4.75 to 5.25 (m, 2H), 3.75 to 4.30 (m, 2H), 3.00 (s, 6H), 0.25 to 2.25 (m, 40H)

Example 7

[Reaction of 9, 10-Diphenylanthracene Adduct (DAP-DPA) and Vitamin D3 (Synthesis of Ene Compound)]
50 mg (0.106 mmol) of 9, 10-diphenylanthracene adduct (DAP-DPA) and 40 mg (0.103 mmol) of vitamin D3 were dissolved in 5 mL of 1,2-dimethoxyethane (DME) to obtain a DME solution. The obtained DME solution was stirred at 70° C. for 5 hours to obtain a reaction solution.
The obtained reaction solution was analyzed using a high performance liquid chromatography (HPLC) under the following conditions, and as result, it was found that 51.4 mg (yield 82.7%) of a vitamin D3 adduct, an ene compound, that is, (5S,7S)-2-[4-(dimethylamino)phenyl]-5-[(E)-[(1R, 3aS,7aR)-1-[(1R)-1,5-dimethylhexyl]octahydro-7a-methyl-4H-indene-4-ylidene]methyl]-5,6,7,8,9,10-hexahydro-7-hydroxy-1H-[1,2,4]triazolo[1,2-b]phthaldine-1,3(2H)-dione was contained. Incidentally, 2.44 mg of vitamin D3 was contained (recovery rate: 6.1%).
(Analysis Conditions)
Sample concentration: 0.05%
Injection volume: 1.0 μL
Wavelength: 254 nm
Flow rate: 1.0 mL/min.

Mobile phase: 0 to 15 min. (CH$_3$CN:water=50:50 to CH$_3$CN:water=100:0)
15 to 20 min. (CH$_3$CN:water=100:0)
Column temperature: 30° C.
Packing material: X Bridge C18 5 μm (4.6×150)
Retention time: Vitamin D3 adduct: 13.2 min.
Vitamin D3: 18.7 min.

[Reaction Scheme]

The reaction scheme carried out in Example 7 is shown below.

g (18.2 mmol; 1.0 eq.) of 9-phenylanthracene, 4.0 g of anhydrous magnesium sulfate, and 400 mL of ethyl acetate, from which dissolved oxygen had been removed by nitrogen-bubbling, were charged and stirred at room temperature. At this time, the reaction mixture changed to a purple suspension, and after 1 hour, it changed to a pink suspension.

After stirring for 24 hours or more, 400 mL of heptane was added to the reaction mixture, and the mixture was concentrated to about 210 g with an evaporator. At this time,

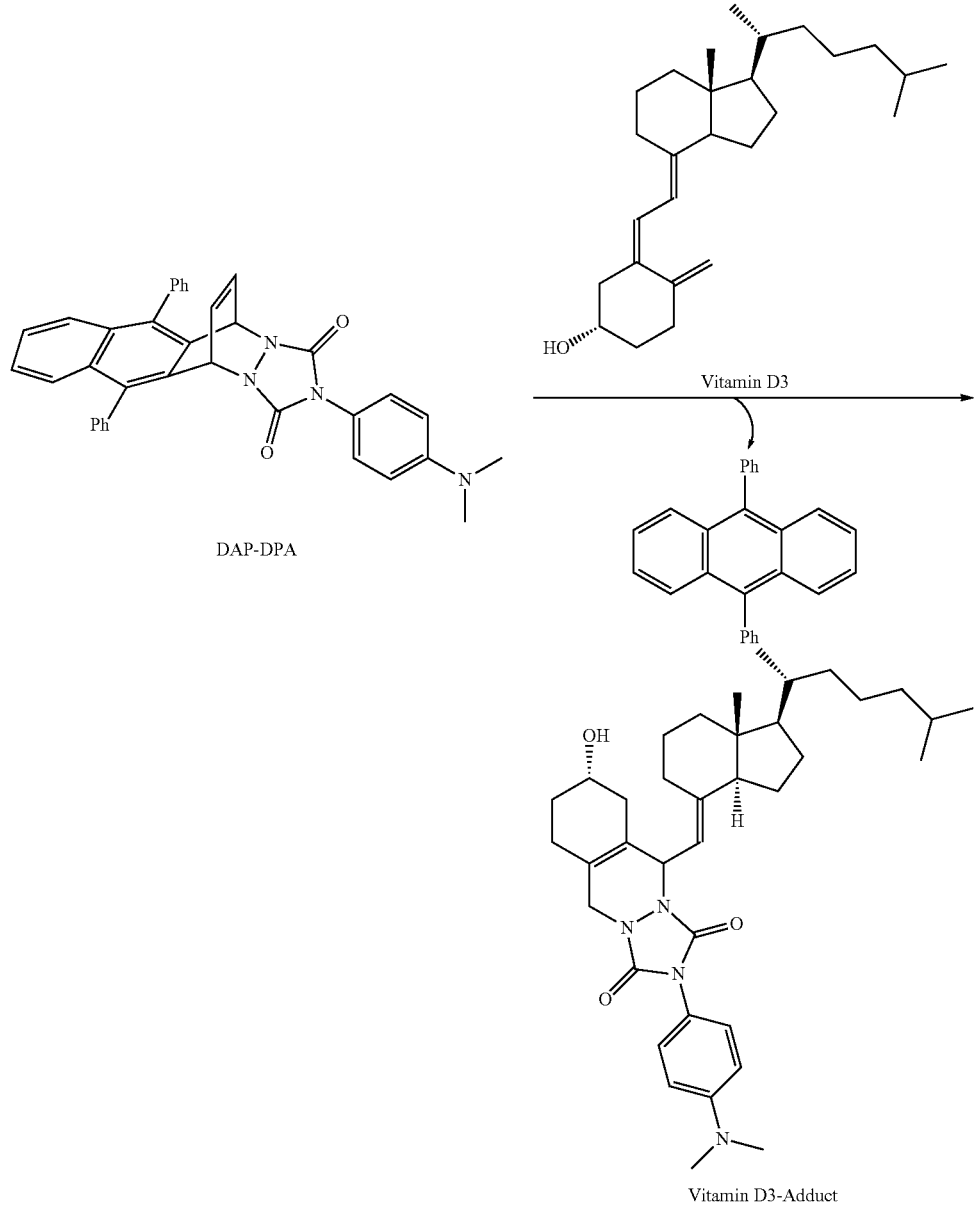

Example 8

[Synthesis of 9-Phenylanthracene Adduct (DAP-PA)]

A reaction apparatus was assembled by attaching a mechanical stirrer and a thermometer to a four-necked 500 mL glass flask. To the flask, 4.00 g (18.2 mmol; 1.0 eq.) of 4-(4'-dimethylaminophenyl)-1,2,4-triazolidine-3,5-dione (DMU), 4.00 g (18.2 mmol; 1.0 eq.) of iodosobenzene, 4.63 precipitation of the adduct occurred and the reaction mixture changed to a slurry-like state.

The obtained slurry was filtered through a Kiriyama funnel (φ60 mm, No. 5A) and washed with 200 mL of hexane. The solid remaining on the filter paper was collected by dissolving in 200 mL of dichloromethane, and the obtained dichloromethane solution was concentrated with an evaporator to obtain a purple solid, and vacuum drying was carried out at room temperature for 15 hours or more to obtain a triazolinedione adduct. The obtained purple solid triazolinedione adduct was a DAPTAD-phenylanthracene adduct (DAP-PA). The amount obtained was 6.30 g, the yield was 73%, and the HPLC purity was 96.0%.

Example 9

[Synthesis of 9-Phenylanthracene Adduct (DAP-PA)]

A reaction apparatus was assembled by attaching a mechanical stirrer and a thermometer to a four-necked 1,000 mL glass flask. To the flask, 10.00 g (45.4 mmol; 1.0 eq.) of 4-(4'-dimethylaminophenyl)-1,2,4-triazolidine-3,5-dione (DMU), 9.99 g (45.4 mmol; 1.0 eq.) of iodosobenzene, 11.55 g (45.4 mmol; 1.0 eq.) of 9-phenylanthracene, 10.0 g of anhydrous magnesium sulfate and 1,000 mL of ethyl acetate from which dissolved oxygen had been removed by nitrogen-bubbling were charged and stirred at room temperature. At this time, the reaction mixture changed to a purple suspension, and after 1 hour, it changed to a pink suspension.

After stirring for 24 hours or more, 1,000 mL of heptane was added to the reaction mixture, and the mixture was concentrated to about 500 g with an evaporator. At this time, precipitation of the adduct occurred and the reaction mixture changed to a slurry-like state.

The obtained slurry was filtered through a Kiriyama funnel (φ60 mm, No. 5A) and washed with 500 mL of hexane. The solid remaining on the filter paper was collected by dissolving in 500 mL of dichloromethane, and the obtained dichloromethane solution was concentrated with an evaporator to obtain a purple solid, and vacuum drying was carried out at room temperature for 15 hours or more to obtain a triazolinedione adduct. The obtained purple solid triazolinedione adduct was a DAPTAD-phenylanthracene adduct (DAP-PA). An amount obtained was 16.52 g, a yield was 77%, and a HPLC purity was 96.4%.

Example 10

[Synthesis of 9-Methylanthracene Adduct (DAP-MA)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 4.36 g (22.7 mmol; 1.0 eq.) of 9-methylanthracene, 5.0 g of anhydrous magnesium sulfate, and 500 mL of ethyl acetate from which dissolved oxygen had been removed by nitrogen-bubbling were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain a red solid, and vacuum drying was carried out at room temperature for 15 hours or more to obtain a triazolinedione adduct. The obtained red solid triazolinedione adduct was a DAPTAD-methylanthracene adduct (DAP-MA). An amount obtained was 6.62 g, a yield was 71%, and a HPLC purity was 96.3%.

Example 11

[Synthesis of 9-Chloromethylanthracene Adduct (DAP-CMA)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 5.15 g (22.7 mmol; 1.0 eq.) of 9-chloromethylanthracene, 5.0 g of anhydrous magnesium sulfate, and 500 mL of ethyl acetate from which dissolved oxygen had been removed by nitrogen-bubbling were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain a reddish-purple solid, and vacuum drying was carried out at room temperature for 15 hours or more to obtain a triazolinedione adduct. The obtained reddish-purple solid triazolinedione adduct was a DAPTAD-chloromethylanthracene adduct (DAP-CMA). An amount obtained was 8.79 g, a yield was 87%, and a HPLC purity was 97.1%.

Example 12

[Synthesis of 9-Bromoanthracene Adduct (DAP-BA)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 5.84 g (22.7 mmol; 1.0 eq.) of 9-bromomethylanthracene, 5.0 g of anhydrous magnesium sulfate, and 500 mL of ethyl acetate from which dissolved oxygen had been removed by nitrogen-bubbling, were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain a reddish-purple solid, and vacuum drying was carried out at room temperature for 15 hours or more to obtain a triazolinedione adduct. The obtained reddish-purple solid triazolinedione adduct was a DAPTADbromoanthracene adduct (DAP-BA). An amount obtained was 8.09 g, a yield was 75%, and a HPLC purity was 96.4%.

Example 13

[Synthesis of 9-Acetylanthracene Adduct (DAP-AcA)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 5.00 g (22.7 mmol; 1.0 eq.) of 9-acetylanthracene, 5.0 g of anhydrous magnesium sulfate, and 500 mL of ethyl acetate, from which dissolved oxygen had been removed by nitrogen-bubbling, were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain a reddish-purple solid, and vacuum drying was carried out at room temperature for 15 hours or more to obtain a triazolinedione adduct. The obtained reddish-purple solid triazolinedione adduct was a DAPTAD-acetylanthracene adduct (DAP-AcA). An amount obtained was 9.36 g, a yield was 94%, and a HPLC purity was 96.7%.

Example 14

[Synthesis of [9-(4'-Dimethylaminophenyl) Anthracene Adduct (DAP-DMAP)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 6.75 g (22.7 mmol; 1.0 eq.) of 9-(4'-dimethylaminophenyl) anthracene, 5.0 g of anhydrous magnesium sulfate, and 500 mL of ethyl acetate, from which dissolved oxygen had been removed by nitrogen-bubbling, were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain a yellow solid, and vacuum drying was carried out at room temperature for 15 hours or more to obtain a triazolinedione adduct. The obtained yellow solid triazolinedione adduct was a DAPTAD-dimethylaminophenylanthracene adduct (DAP-DMAPA). An amount obtained was 7.96 g, a yield was 68%, and a HPLC purity was 96.9%.

Example 15

[Synthesis of [9-(4'-nitrophenyl)anthracene Adduct (DAP-NPA)]

A reaction apparatus was assembled by attaching a mechanical stirrer and a thermometer to a four-necked 500 mL glass flask. To the flask, 5.00 g (22.7 mmol; 1.0 eq.) of 4-(4'-dimethylaminophenyl)-1,2,4-triazolidine-3,5-dione (DMU), 5.00 g (22.7 mmol; 1.0 eq.) of iodosobenzene, 6.80 g (22.7 mmol; 1.0 eq.) of 9-(4'-nitrophenyl) anthracene, 5.0 g of anhydrous magnesium sulfate, and 500 mL of ethyl acetate, from which dissolved oxygen had been removed by nitrogen-bubbling, were charged and stirred at room temperature. At this time, the reaction mixture changed to a purple suspension, and after 1 hour, it changed to a pale reddish-purple suspension.

After stirring for 24 hours or more, 500 mL of heptane was added to the reaction mixture, and the mixture was concentrated to about 250 g with an evaporator. At this time, precipitation of the adduct occurred and the reaction mixture changed to a slurry-like state.

The obtained slurry was filtered through a Kiriyama funnel (φ60 mm, No. 5A) and washed with 250 mL of hexane. The solid remaining on the filter paper was collected by dissolving in 250 mL of dichloromethane, and the obtained dichloromethane solution was concentrated with an evaporator to obtain an orange solid, and vacuum drying was carried out at room temperature for 15 hours or more to obtain a triazolinedione adduct. The obtained orange solid triazolinedione adduct was a DAPTAD-nitrophenylanthracene adduct (DAP-NPA). An amount obtained was 8.46 g, a yield was 72%, and a HPLC purity was 97.2%.

Example 16

[Purification of 9-Phenylanthracene Adduct (DAP-PA)]

A glass column (φ5.4 cm×60 cm) was wet-packed with 150 g of silica gel (Wakosil C-300; Fuji Film Wako). Hexane/ethyl acetate=7/3 was used as a packing solvent.

3.00 g of a purple solid DAPTAD-phenylanthracene adduct (DAP-PA), obtained in Example 9, was dissolved in 10 mL of chloroform and charged onto a column. Thereafter, development was carried out using hexane/ethyl acetate=7/3.

A fraction of 400 mL containing a spot of the target adduct was concentrated with an evaporator, then vacuum drying was carried out for 15 hours or more to obtain the DAPTAD-phenylanthracene adduct (DAP-PA) as a white solid. The amount obtained was 1.02 g, the yield was 34%, and the HPLC purity was 98.2%.

Example 17

[Purification of 9-phenylanthracene Adduct (DAP-PA)]

A glass column (φ5.4 cm×60 cm) was wet-packed with 150 g of silica gel (Wakosil C-300; Fuji Film Wako). Hexane/tetrahydrofuran=5/5 was used as a packing solvent.

3.00 g of a purple solid DAPTAD-phenylanthracene adduct (DAP-PA), obtained in Example 9, was dissolved in 10 mL of chloroform and charged onto a column. Thereafter, development was carried out using hexane/tetrahydrofuran=5/5.

A fraction of 600 mL containing a spot of the target adduct was concentrated with an evaporator, then vacuum drying was carried out for 15 hours or more to obtain the DAPTAD-phenylanthracene adduct (DAP-PA) as a white solid. The obtained amount was 1.55 g, yield was 52%, and a HPLC purity was 98.8%.

Example 18

[Obtainment of DAPTAC by Adding PIDA to Mixed Solution of DMU and TTB]

0.10 g (0.45 mmol) of 4-(4'-dimethylaminophenyl)-1,2,4-triazolidine-3,5-dione (DMU) and 0.09 g (0.43 mmol) of trans,trans-diphenylbutadiene (TTB) were added to 100 mL of 1,2-dimethoxyethane (DME) to obtain a DME suspension.

To the obtained suspension, 0.15 g (0.46 mmol) of iodobenzen diacetate (PIDA) was added at 20° C. and stirred at the same temperature for 4 hours to obtain a reaction solution containing cis-2-(4-dimethylaminophenyl)-5,8-diphenyl-1H-[1,2,4]triazolo[1,2-a]pyridazine-1,3(2H)-dione (DAPTAC).

With respect to the obtained reaction solution, a high performance liquid chromatography (HPLC) analysis was carried to calculate an assay yield of DAPTAC under the following conditions. The assay yield of DAPTAC was 76.8%.

(Analysis Conditions)
  Sample concentration: 50%
  Injection volume: 1.0 μL
  Wavelength: 254 nm
  Flow rate: 1.0 mL/min.
  Mobile phase: 0 to 15 min. (CH$_3$CN:water=50:50 to CH$_3$CN:water=100:0)
  15 to 20 min. (CH$_3$CN:water=100:0)
  Column temperature: 30° C.
  Packing material: X Bridge C18 5 μm (4.6×150) Retention time: DMU: 2.1 min.
  DAPTAC: 7.2 min.
  TTB: 11.4 min.

[Reaction Scheme]

The reaction scheme carried out in Example 18 is shown below.

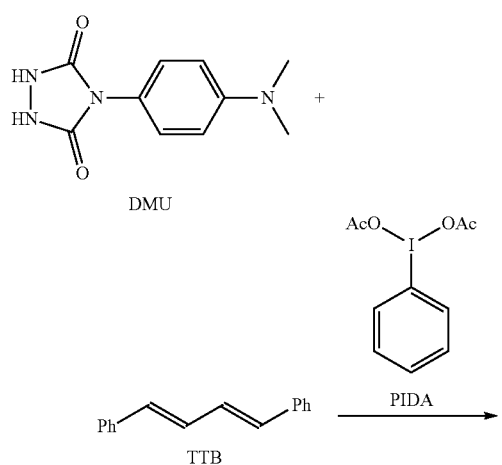

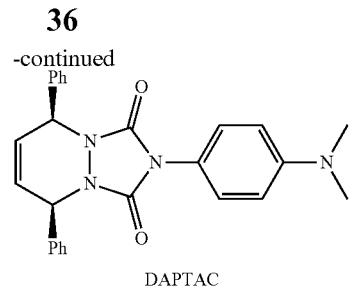

DAPTAC

[Isolation of DAPTAC]

The obtained reaction solution was successively washed with a 5% aqueous sodium bicarbonate solution, followed by water, and concentrated under reduced pressure. The concentrated residue was purified by a silica gel column chromatography (eluting solvent: ethyl acetate). After concentrating the fraction containing the product under reduced pressure, the concentrated residue was heated and dispersed with 10 mL of ethyl acetate and cooled at room temperature to precipitate crystals. The precipitated crystals were filtered, washed with hexane, and dried under reduced pressure to obtain DAPTAC in a solid state.

[Evaluation of Physical Properties]

Various analyses were carried out on the resultant DAPTA. The results are shown below.

Mp: 174 to 177° C.
IR (KBr): 1772, 1700 cm$^{-1}$
$^1$H-NMR (CDCl$_3$): δ 7.10-7.75 (m, 12H), 6.50-6.85 (m, 2H), 6.00 (s, 2H), 5.51 (s, 2H), 2.90 (s, 6H)

Example 19

[Obtainment of Vitamin D3 Adduct by Adding PIDA to Mixed Solution of DMU and Vitamin D3]

0.01 g (0.045 mmol) of 4-(4'-dimethylaminophenyl)-1,2,4-triazolidine-3,5-dione (DMU) and 0.017 g (0.044 mmol) of vitamin D3 were added to 10 mL of 1,2-dimethoxyethane (DME) to obtain a DME suspension.

To the obtained suspension, 0.015 g (0.045 mmol) of iodobenzene diacetate (PIDA) was added at 20° C. and stirred at the same temperature for 3 hours to obtain a reaction solution containing (5S,7S)-2-[4-(dimethylamino)phenyl]-5-[(E)-[(1R,3aS,7aR)-1-[(1R)-1,5-dimethylhexyl] octahydro-7a-methyl-4H-indene-4-ylidene]methyl]-5,6,7,8,9,10-hexahydro-7-hydroxy-1H-[1,2,4]triazolo[1,2-b] phthalazine-1,3(2H)-dione (vitamin D3 adduct).

With respect to the obtained reaction solution, a high performance liquid chromatography (HPLC) analysis was carried out to calculate an assay yield of the vitamin D3 adduct under the following conditions. The assay yield of the vitamin D3 adduct was 84.3%.

(Analysis Conditions)
  Sample concentration: 50% (Measurement was made by diluting the reaction solution with the same weight of THF.)
  Injection volume: 1.0 μL
  Wavelength: 254 nm
  Flow rate: 1.0 mL/min.
  Mobile phase: 0 to 15 min. (CH$_3$CN:water=50:50 to CH$_3$CN:water=100:0)
  15 to 20 min. (CH$_3$CN:water=100:0)
  Column temperature: 30° C.
  Packing material: X Bridge C18 5 μm (4.6×150)
  Retention time: DMU: 2.1 min.
  Vitamin D3 adduct: 13.2 min.
  Vitamin D3: 18.8 min.

37

[Reaction Scheme]

The reaction scheme carried out in Example 19 is shown below.

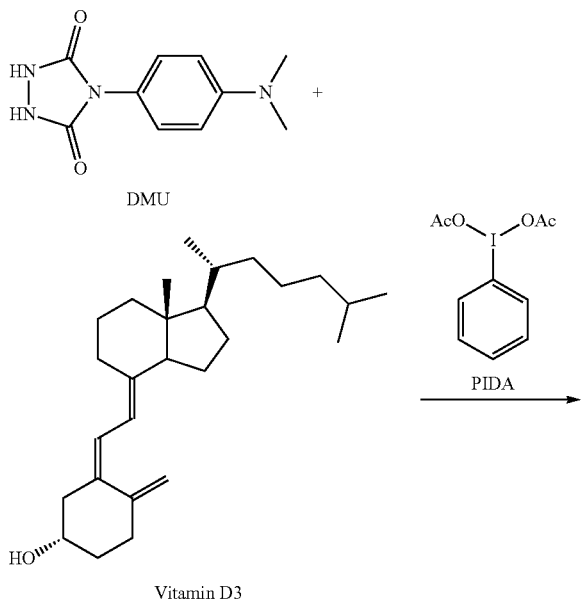

[Isolation of Vitamin D3 Adduct]

The obtained reaction solution was successively washed with a 5% aqueous sodium bicarbonate solution, followed by water, and concentrated under reduced pressure. The concentrated residue was purified by a silica gel column chromatography (eluting solvent: hexane/ethyl acetate=4/1, 2/1) to obtain the vitamin D3 adduct.

[Evaluation of Physical Properties]

Various analyses were carried out on the resultant vitamin D3 adduct. The results are shown below.

Mp: 125 to 129° C.

IR (KBr): 1762, 1697 cm$^{-1}$ $^1$H-NMR (CDCl$_3$): δ 7.25 (d, J=15 Hz, 2H), 6.75 (d, J=15 Hz, 2H), 4.75-5.25 (m, 2H), 3.75-4.30 (m, 2H), 3.00 (s, 6H), 0.25-2.25 (m, 40H)

38

Comparative Example 1

[Obtainment of DAPTAC by Obtaining DAPTAD Solution from DMU and PIDA and Adding TTB Thereto]

0.30 g (1.36 mmol) of 4-(4'-dimethylaminophenyl)-1,2,4-triazolidine-3,5-dione (DMU) was added to 10 mL of 1,2-dimethoxyethane (DME) to obtain a DME suspension.

To the obtained DME suspension, 0.44 g (1.36 mmol) of iodobenzen diacetate (PIDA) was added at 20° C. and stirred at the same temperature for 3 hours to obtain a reaction solution containing 4-(4'-dimethylaminophenyl)-1,2,4-triazoline-3,5-dione (DAPTAD).

To the obtained reaction solution containing DAPTAD, 0.28 g (1.36 mmol) of trans, trans-diphenylbutadiene (TTB) was added at 20° C. and stirred at the same temperature for 2 hours to generate DAPTAC.

The obtained reaction solution was subjected to the same HPLC analysis as in Example 18, and the assay yield of DAPTAC was found to be 31.1%.

[Reaction Scheme]

The reaction scheme carried out in Comparative Example 1 is shown below.

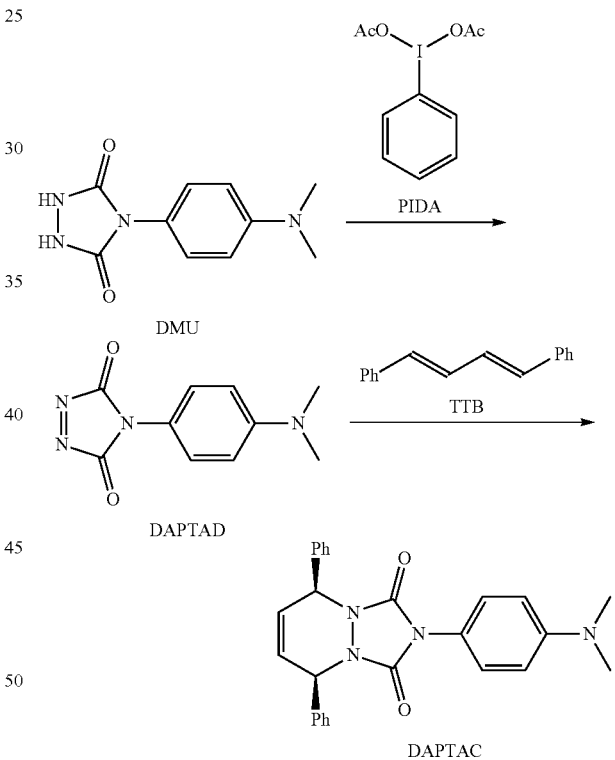

Example 20

[Obtainment of Anthracene Adduct by Adding PIO to Mixed Solution of DMU and Anthracene]

81 mg (0.45 mmol) of anthracene was weighed into a light-shielding vessel, and dry acetonitrile (10 mL) was added thereto to dissolve the anthracene. Further, 100 mg (0.45 mmol) of 4-(4'-dimethylaminophenyl)-1,2,4-triazolidine-3,5-dione (DMU) was added, then 110 mg (0.50 mmol) of iodosobenzene was added and the mixture was stirred at room temperature for 4 hours. The obtained suspension was filtered, and the obtained crystals were washed with hexane and dried to obtain an anthracene adduct (DAP-A). An amount of the obtained anthracene adduct (DAP-A) was 75 mg and the yield was 41.7%.

[Reaction Scheme]

The reaction scheme carried out in Example 20 is shown below.

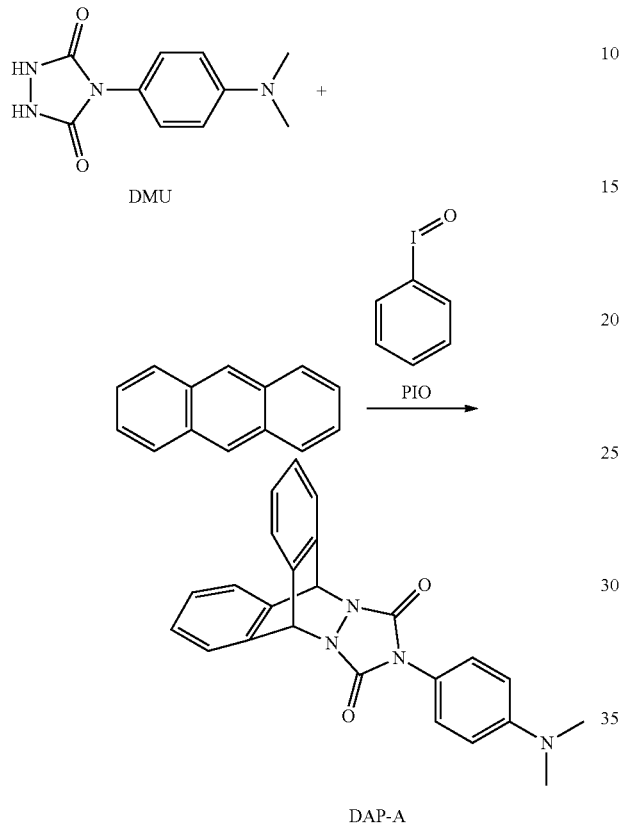

[Evaluation of Physical Properties]

Various analyses were carried out on the resultant anthracene adduct (DAP-A). The results are shown below.

Mp: 217 to 218° C.

IR (KBr): 1780, 1717 cm$^{-1}$ $^1$H-NMR (CDCl$_3$): δ 7.20-7.75 (m, 8H), 6.50-7.15 (m, 4H), 6.25 (s, 2H), 3.00 (s, 6H)

The invention claimed is:

1. A Cookson-type derivatization reagent consisting of a triazolinedione adduct represented by the following formula (2) or (3):

(2)

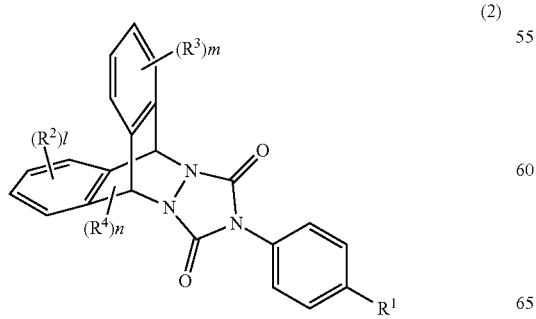

wherein $R^1$ represents a dialkylamino group or a dialkylaminoalkyl group; $R^2$, $R^3$, and $R^4$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; l and m are each independently an integer of 0 to 4; and when $R^4$ is an optionally substituted phenyl group, n is an integer of 0 to 1, and when $R^4$ is a substituent selected from the group consisting of an optionally substituted alkyl group having 1 to 20 carbon atoms, an optionally substituted aralkyl group, an optionally substituted alkenyl group, an optionally substituted acyl group, a halogen group, an optionally substituted amino group, a nitro group, and an optionally substituted heterocyclic group, n is an integer of 0 to 2, (3)

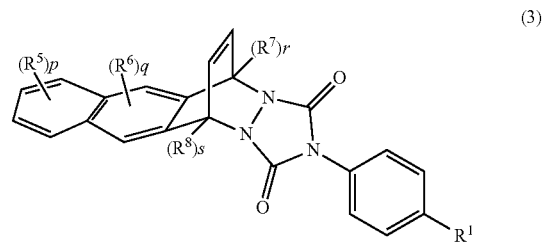

wherein $R^1$ represents a dialkylamino group or a dialkylaminoalkyl group; $R^5$, $R^7$, and $R^8$ each independently represent a substituent selected from the group consisting of an optionally substituted alkyl group having 1 to 20 carbon atoms, an optionally substituted aralkyl group, an optionally substituted alkenyl group, an optionally substituted phenyl group, an optionally substituted acyl group, a halogen group, an optionally substituted amino group, a nitro group, and an optionally substituted heterocyclic group; $R^6$ is an optionally substituted phenyl group; p is an integer of 0 to 4; q is an integer of 2; and r and s are integers of 0 or 1.

2. The Cookson-type derivatization reagent according to claim 1, wherein the Cookson-type derivatization reagent is represented by the following formula (2-1) or (2-2):

(2-1)

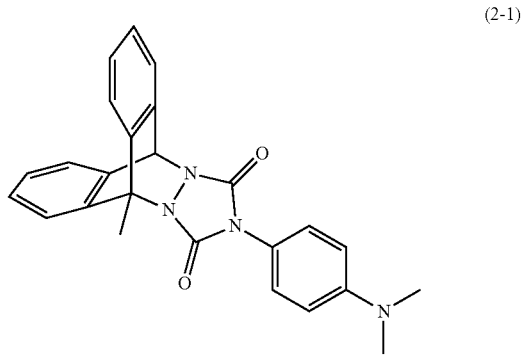 [SMILES: CN(C)c1ccc(-n2c(=O)n3n(c2=O)C2(C)c4ccccc4C3c3ccccc32)cc1]

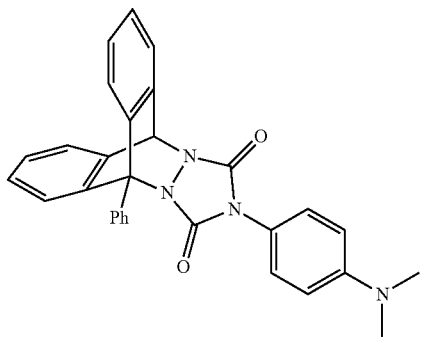

(2-2)

wherein Ph represents a phenyl group.

3. The Cookson-type derivatization reagent according to claim 1, wherein the Cookson-type derivatization reagent is represented by the following formula (3-1):

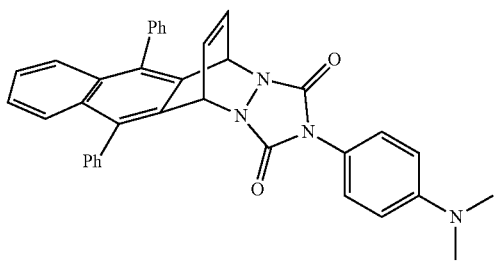

(3-1)

wherein Ph represents a phenyl group.

4. A method for producing the Cookson-type derivatization reagent according to claim 1, comprising subjecting a triazolinedione compound and a compound having an anthracene ring to a Diels-Alder reaction to obtain the triazolinedione adduct, wherein the triazolinedione compound is represented by the following formula (4):

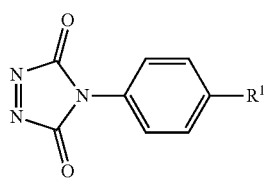

(4)

wherein $R^1$ represents a dialkylamino group or a dialkylaminoalkyl-group.

5. The method according to claim 4, wherein the method further comprises a purification step of purifying the triazolinedione adduct.

6. A method for producing the Cookson-type derivatization reagent according to claim 1, comprising reacting a triazolidinedione compound with a compound having an anthracene ring in the presence of an oxidizing agent to obtain the triazolinedione adduct, wherein the triazolidinedione compound is represented by the following formula (7):

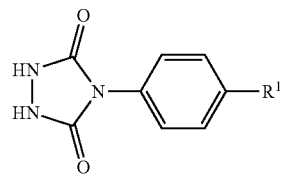

(7)

wherein $R^1$ represents a dialkylamino group or a dialkylaminoalkyl group.

7. The method according to claim 6, wherein the oxidizing agent is a hypervalent iodine compound.

8. The method for according to claim 6,
wherein the oxidizing agent is a hypervalent iodine compound represented by the following formula (8):

(8)

wherein X and Y together represent an oxygen atom, or X and Y each independently represent a group selected from the group consisting of a hydroxy group, an alkoxy group, an acyloxy group, an acylamino group, a tosylamino group, a mesylamino group, a sulfonyloxy group, and a halogen group; and Ar represents a group selected from the group consisting of a phenyl group, a heterocyclic group, and a phenyl group substituted with an alkyl group, an alkoxy group, and a halogen group.

9. The method according to claim 6, wherein the method further comprises a purification step of purifying the triazolinedione adduct.

10. A method for producing an ene compound, comprising reacting a Cookson-type derivatization reagent to obtain the ene compound, wherein the Cookson-type derivatization reagent according to claim 1 is reacted with vitamin D3, 25-hydroxyvitamin D3, or 1,4-diphenylbutadiene at a temperature of 20 to 350° C.

11. A method for analyzing an ene compound, comprising reacting a Cookson-type derivatization reagent to obtain the ene compound and analyzing the ene compound, wherein the Cookson-type derivatization reagent according to claim 1 is reacted with vitamin D3, 25-hydroxyvitamin D3, or 1,4-diphenylbutadiene at a temperature of 20 to 350° C.

12. The method for analyzing an ene compound according to claim 11,
wherein the method uses a high performance liquid chromatography.

* * * * *